(12) United States Patent
Verdin et al.

(10) Patent No.: US 7,232,685 B2
(45) Date of Patent: Jun. 19, 2007

(54) CELL LINES WITH LATENT IMMUNODEFICIENCY VIRUS AND METHODS OF USE THEREOF

(75) Inventors: Eric Verdin, San Francisco, CA (US); Albert Jordan, San Francisco, CA (US)

(73) Assignee: The Regents of the Universtiy of California, Oakland, CA (US)

( * ) Notice: Subject to any disclaimer, the term of this patent is extended or adjusted under 35 U.S.C. 154(b) by 681 days.

(21) Appl. No.: 10/323,463

(22) Filed: Dec. 18, 2002

(65) Prior Publication Data

US 2003/0157693 A1 Aug. 21, 2003

Related U.S. Application Data

(60) Provisional application No. 60/341,727, filed on Dec. 19, 2001.

(51) Int. Cl.
*C12N 5/06* (2006.01)
(52) U.S. Cl. .................. 435/363; 424/188.1; 424/208.1
(58) Field of Classification Search ............. 424/188.1, 424/208.1, 199.1; 435/325, 320.1
See application file for complete search history.

(56) References Cited

U.S. PATENT DOCUMENTS

| | | | |
|---|---|---|---|
| 5,256,534 A | 10/1993 | Butera et al. | |
| 5,459,056 A | 10/1995 | Powell et al. | |
| 6,225,048 B1 * | 5/2001 | Soderberg-Naucler et al. . | 435/5 |

OTHER PUBLICATIONS

Chen, B. K., et al., 1994, Distinct modes of human immunodeficiency virus type 1 proviral latency revealed by superinfection of nonproductively infected cell lines with recombinant luciferase-encoding viruses, J. Virol. 68(2):654-660.*
Lewinski et al., "Genome-Wide Analysis of Chromosomal Features Repressing Human Immunodeficiency Virus Transcription", Journal of Virology, 2005, vol. 79, No. 11, pp. 6610-6619.
Valerie K et al. "Activation of human immunodeficiency virus type 1 by DNA damage in human cells" Nature 1988, pp. 78-81.
Latham P S et al. "Expression of Human Immunodeficiency Virus Long Terminal Repeat in the Human Promonocyte Cell Line U937 Effect of Endotoxin and Cytokines" Cellular Immunology, vol. 129, No. 2. 1990, pp. 513-518.
Jordan Albert et al. "The site of HIV-1 Integration in the human genome determines basal transcriptional activity and response to Tat transactivation" EMBO (European Molecular Biology Organization) Journal, vol. 20, No. 7, Apr. 2001, pp. 1726-1738.
Chen Benjamin K et al. "Distinct modes of human immunodeficiency virus type 1 proviral latency revealed by superinfection of nonproductively infected cell lines with recombinant luciferase-encoding viruses" Journal of Virology, The American Society for Microbiology, US, vol. 68, No. 2, Feb. 1994, pp. 654-660.
Van Lint Carine et al. "Transcriptional activation and chromatin remodeling of the HIV-1 promoter in response to the histone acetylation" EMBO (European Molecular Biology Organization) Journal, vol. 15, No. 5, 1996, pp. 1112-1120.
Verdin Eric et al. "A new in vitro model for HIV latency" Journal of Human Virology, vol. 5, No. 1, Jan. 2002, p. 60 & 2002 International Meeting of the Institute of Human Virology; Baltimore, Maryland, USA; Sep. 9-13, 2002.
Sylvie Legrand-Poels et al. "Activation of Human Immunodeficiency Virus Type 1 by Oxidative Stress", Aids Research and Human Retroviruses 1990 vol. 6, No. 12, pp. 1389-1397, abstract, Figure 4, and 1395, col. 1, last paragraph.
Bakri, Y. et al. The Maturation of Dendritic Cells Results in Postintegration Inhibition of HIV-1 Replicon. They Journal of Immunology. 2001 vol. 166, pp. 3780-3788, see abstract, and pp. 3781-2782.
Jordan, A et al. "Hiv Reproducibly Establishes a Latent Infection After Acute Infection of T Cells In Vitro", The EMBO Journal, 2003, vol. 22, No. 8, pp. 1868-1877.
Kulkosky et al. (2001) *Blood*, 98:3006-3015.
Emiliani et al. (1996) *Proc. Natl. Acad. Sci. USA* 93:6377-6381.
Emiliani et al. (1998) *J. Virol.* 72:1666-1670.
Antoni et al. (1994) *Virol.* 202:684-694.
Carteau et al. (1998) *J. Virol.* 72:4005-4014.

* cited by examiner

*Primary Examiner*—Jeffrey S. Parkin
(74) *Attorney, Agent, or Firm*—Paula A. Borden; Bozicevic, Field & Francis LLP

(57) ABSTRACT

The present invention provides isolated cells that comprise, integrated into the genome of the cell, a transcription-competent immunodeficiency virus or a transcription-competent immunodeficiency virus-based retroviral vector. Under basal in vitro culture conditions, the immunodeficiency virus is latent, and the expression of the latent immunodeficiency virus can be reactivated. The invention further provides methods of making a subject cell. The invention further provides screening methods for identifying agents that activate a latent immunodeficiency virus; and screening method for identifying agents that block reactivation of latent immunodeficiency virus expression in response to T cell activation signals. The invention further provides agents identified in the subject screening assays. The invention further provides methods of treating an immunodeficiency virus infection.

13 Claims, 13 Drawing Sheets

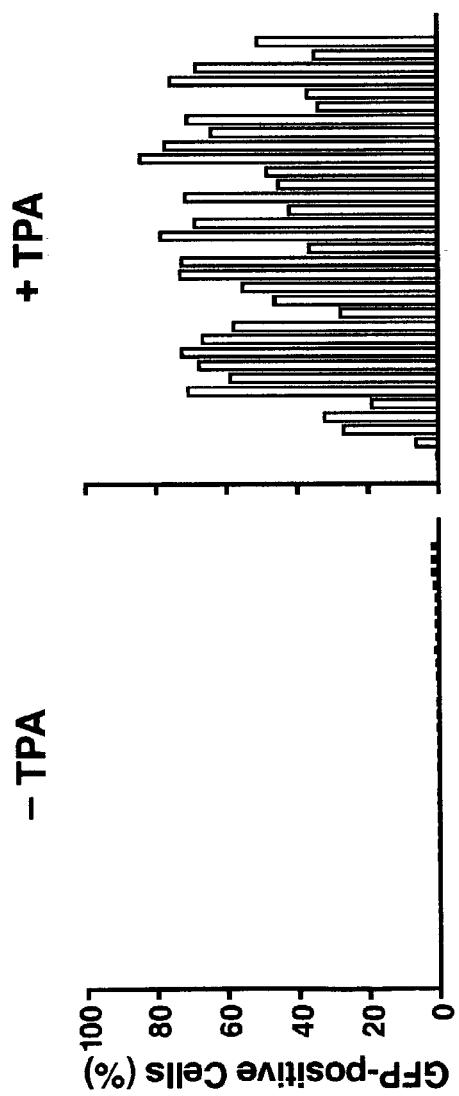
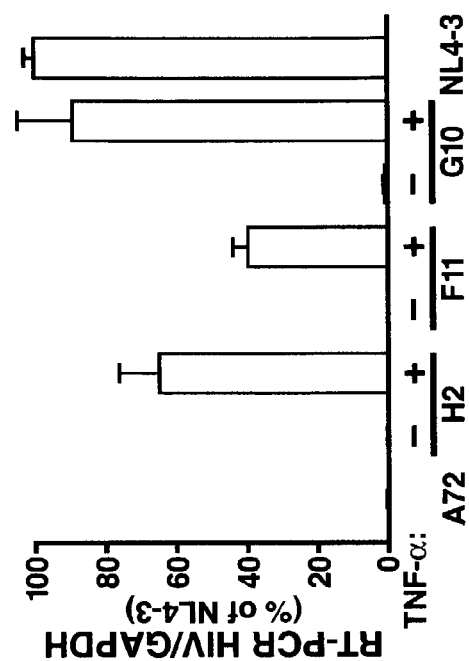
FIG. 1B
FIG. 1C

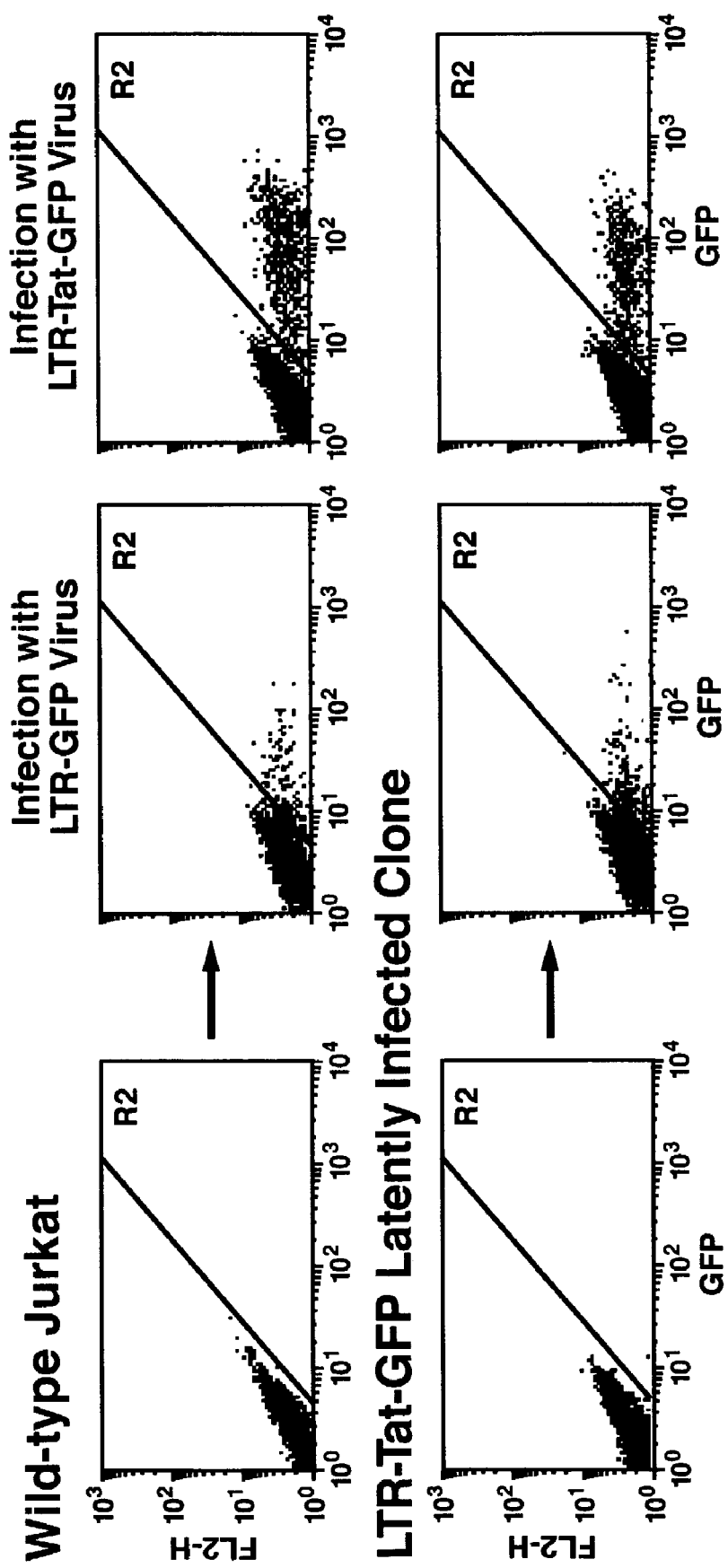

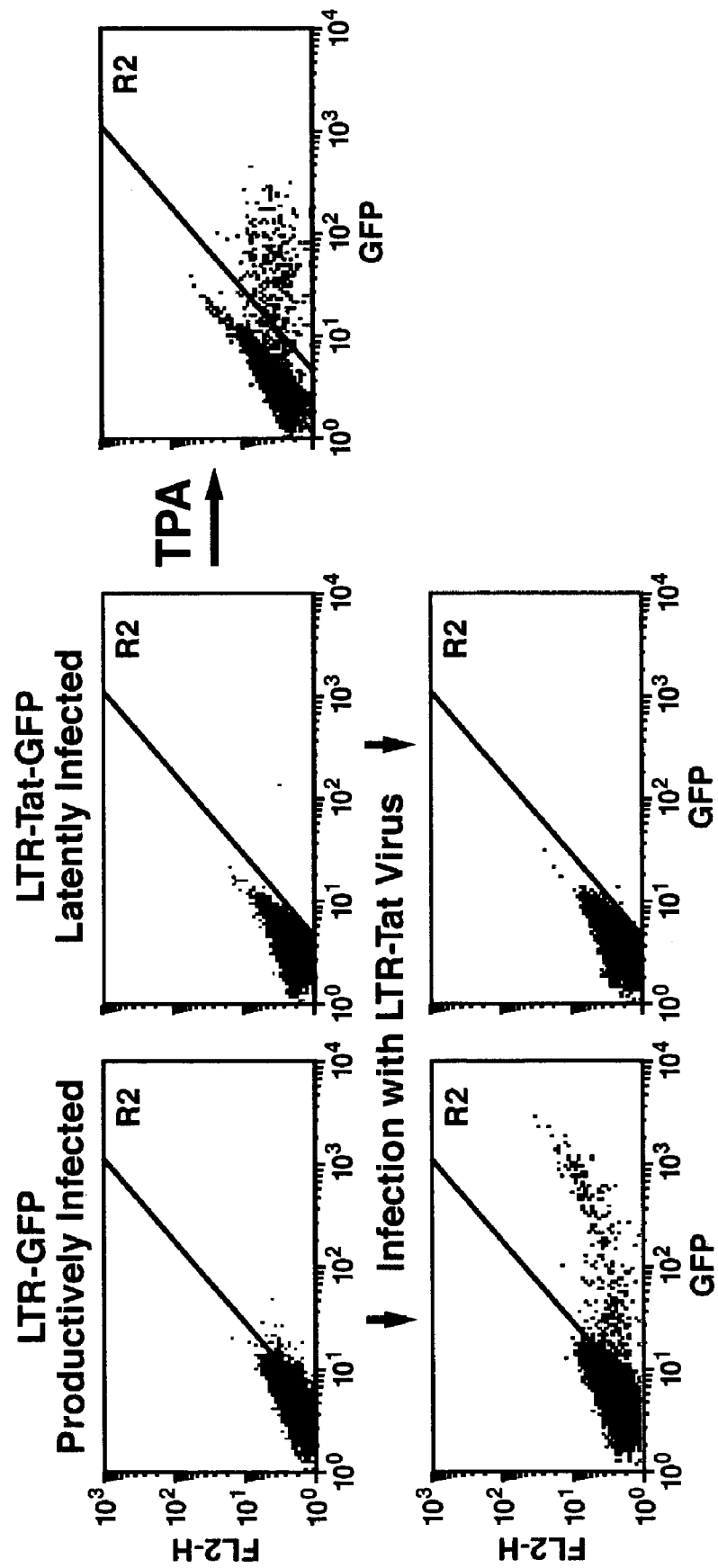

FIG. 3A

| Name | Sequence | 5' LTR | Alphoid Repeat | Location | PCR |
|---|---|---|---|---|---|
| Clone 82 | ATGTGTGCGTTCAACTCACACAGAGTTTAACCTTTCTTTCTTTCCTAGAGCAGTGGAAGGGCTAATTCACTCCC (SEQ ID NO:33)<br>\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|<br>ATGTGTGCGTTCAACTCACACAGAGTTTAACCTTTCTTTCTTTCGTAGAGCAG (SEQ ID NO:34) | | Alphoid Repeat | CHR 10 | + |
| Clone A1 | AGCTTCCTGACTATGATAAAGTATCTTGTGAAAAAACCAATGTTACTGCTTGGAAGGGCTAATTCACTCCC (SEQ ID NO:35)<br>\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|<br>AGCTTCCTGACTATGATAAAGTATCTTGTGAAAAACCAATGTTACTGTTACTGCT (SEQ ID NO:36) | | — | CHR X | — |
| Clone A5 | CGGCTCACTGCAGCCTCCGCCTCTCGAATTCAATTCTGTCTCAGCCCTCTGGAAGGGCTAATTCACTCCC (SEQ ID NO:37)<br>\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|<br>CGGCTCACTGCAGCCTCCGCCTCTCGAATTCAATTCTGTCTCAGCCTC (SEQ ID NO:38) | | — | CHR 8 | — |
| Clone A7 | CTGTGATTTGAATGCACACATCACAAAGAAGTTTCTCAGAATGCTTCTTGGAAGGGCTAATTCACTCCC (SEQ ID NO:39)<br>\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|<br>CTGTGATTTGAATGCACACATCACAAAGAAGTTTCTCAGAATGCTTCT (SEQ ID NO:40) | | Alphoid Repeat | CHR 7 | + |
| Clone A10 | GAGTTGACAAAGGTAAAACAGATTTTTTAAAAAATCAGTGTTTATATTGGAAGGGCTAATTCACTCCC (SEQ ID NO:41)<br>\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|<br>GAGTTGACAAAGGTAAAACAGATTTTTTAAAAAATCAGTTGTTTATATT (SEQ ID NO:42) | | — | CHR 9 | — |
| Clone H2 | CTGTGATTTGAATGCACACAGAATGATTCTCAGAAACTACTTTGTGAAGGGCTAATTCACTCCC (SEQ ID NO:43)<br>\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|<br>CTGTGATTTGAATGCACACAGAATGATTCTCAGAAACTACTTTCT (SEQ ID NO:44) | | Alphoid Repeat | CHR 7 | + |
| Clone F2 | TTCGTAGGAGAACTAGACAGAATGATTCTCAGAAACTACTTTGTGATGGGAAGGGCTAATTCACTCCC (SEQ ID NO:45)<br>\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|<br>TTCGTAGGAGAACTAGACAGAATGATTCTCAGAAACTACTTTGTGATG (SEQ ID NO:46) | | Alphoid Repeat | CHR 16 | + |

FIG. 6

Boxed sequences are LTR;
all other sequences are genomic sequences
corresponding to integration site

Patient #1

AAAGAGTGTTTCCAAGCTGCTCTGTCAAAAGGAAGGTTCTTCTCTGTTAGGTGAGTGCAT
ACGTCATAAAGGAGTTTCTGAGAATTCTTCTGTCTAGTTCTTATTTGTAGACGTTTCCTT
TCTCACCTTAGGCCTGAAAGCGCTCGAAATATCCACTTCCAGATAGTACAGAAATAGTGA
TTCAAACCTGGAAGGGCTAATTCAC (5' LTR) (SEQ ID NO:47)

Patient #2

(3' LTR) GACCCTTTTAGTCAGTGTGGAAAATCTCTAGCAAAAGGGTGTTTCAAACC
TGCTCTATGAAAGGGAATGTTCAACTCTGTGACNTTGAATGCAAATATCACAAAGAAGTT
ACTGGGAATGCTGCTGTCTGCTTTTTATATGTAATCCCGTTTCCAACGAAATCCTCAAAG
CTAGACAAATATCCACTTGCAGATTCCACAAAAAGAGTGTTTCAAATCTGCTCAATCAAA
(SEQ ID NO:48)

Patient #3

(3' LTR) TCTGGTCCCTGGCCCTGGTGTGTAGTTCTGCCAATCAGGGAAGTAGCCTTG
TGTGTGGTAGACCCACAGATCAAGAATATCTTGTCTGTTCTGGGAGTGAACTAGCCCTTC
CACCTGCATGTGGAAATTTTGAGCGCTTTGAGGCCTATTGTGGAAAAGGAAATATGTTCA
CATAAAAGCTACACAGAAGCATTCTGAAAAACGTCTTTGTGATGAGTGCATTCATCTCAC
AGAGTTGATCCTTTCTTTTTATTCAGCAGTTTTGAAACACTCCTTTTAGAGAATCTGCAA
GTAGATATTTGGAGCGCGTTGAGGCCTACCATGGAAAAGCAAATATCTTCACATAAAAAC
TACACAGAAATATTCTCAGAAACTACTTTGTGATATGTGTGTTCAATTCACAGAGTTGAA
CCTTTCTTTTCATTGAGCAGTTTTGAAAAACTGCTTTTCTAGAATCTGCTTGTGGATATT
TGGAGCTCTTTGAGGAATTCATTGTCAATGGGATATCTTCATATACAAACTAGCCAGAAG
CATTCTCAGAAACTACTTTGTGATCCTGAATTCCAGCAC (SEQ ID NO:49)

Patient #4

(3' LTR) AGTCCCTGGCCCTGGTGTGTAGTTCTGCCAATCAGGGAAGTAGCCTTGTGT
GTGGTAGACCCACAGATCAAGAATATCTTGTCTTTTCTGGGAGTAAATTAGCCCTTCCAG
ATATTAACTTTTCAAACATAGGCCGCACAGTGATCCAAATATGTACCTTACAGATACTTC
AAAAAGACTGTTTCCAACCTGCTCAATGAAAGAAAGTTTCAACTGTGTGAGTGGAATGC
AAACATCACAAAGAAGTTTCTCAGAATGCCCCTGTCAACTTTATATGTGAAGATATTGCC
TTTTCCACAAAACGCCTCAAACCATTCCAAATATCCATTTGCAGATTCCACAAAAAGACT
GTTTCCAAACTGCTCAACCAAAAAAAGGTTCAACTCTGTGAGATGAATGCACCCATCACA
AAGAAGTTTTTCAGAAAGCTTCTGTTTAGTTTTTATGTGAAGATATTTCCTTTTTCACTA
TAGGCTTCAAAGCACTCCACACATCCATTTGCAGATTCTACAAAAGAGTGTTTCCAATCT
GCTNCCTGAATTNCAGCACACTGGCGGCCGTTACTAGT (SEQ ID NO:50)

CELL LINES WITH LATENT IMMUNODEFICIENCY VIRUS AND METHODS OF USE THEREOF

CROSS-REFERENCE

This application claims the benefit of U.S. Provisional Patent Application No. 60/341,727 filed Dec. 19, 2001, which application is incorporated herein by reference in its entirety.

STATEMENT REGARDING FEDERALLY SPONSORED RESEARCH

This invention was made with government support under grant nos. ROI-GM51671-05A2 awarded by the National Institutes of Health. The government may have certain rights in this invention.

FIELD OF THE INVENTION

This invention is in the field of immunodeficiency viruses, particularly recombinant immunodeficiency viruses, and cell lines containing same.

BACKGROUND OF THE INVENTION

Combination antiretroviral therapy can control HIV-1 replication and delay disease progression. However, despite the complete suppression of detectable viremia in many patients, viremia reemerges rapidly after interruption of treatment, consistent with the existence of a latent viral reservoir. This reservoir is thought to consist mainly of latently infected resting memory CD4+ T cells. Due to the long half-life of this reservoir (44 months), it has been estimated that its total eradication with current treatment would require over 60 years.

Latently infected cells contain replication-competent integrated HIV-1 genomes that are blocked at the transcriptional level, resulting in the absence of viral protein expression. HIV depends on both cellular and viral factors for efficient transcription of its genome, and the activity of the HIV promoter is tightly linked to the level of activation of its host cell. It is thought that reactivation of latently infected memory T cells by their cognate antigen leads to a reactivation of viral gene expression and the completion of the viral life cycle. However, it is not clear how the latent state is established. It has been proposed that latency occurs when an activated T cell in the early stage of infection returns to a quiescent state, leading to suppression of viral transcription until the cell becomes reactivated. However, the infected cell would need to survive the cytopathic effects of infection to effectively transition to the resting state. Alternatively, an activated, infected cell could become quiescent before the onset of viral expression and the occurrence of cytopathic effects, as has been reported during thymopoiesis. The unlikely coincidence of these two events could account for the low frequency of latently infected cells in vivo (~$10^6$ cells per infected individual).

HIV transcription is characterized by two temporally distinct phases. The early phase occurs immediately after integration and relies solely on cellular transcription factors. Because of a transcriptional elongation defect in the basal HIV promoter, most transcripts cannot elongate efficiently and terminate rapidly after initiation. This process leads to the accumulation of short transcripts at the 5' region of the viral genome containing the TAR element. However, the elongation defect is not absolute, and a few transcripts elongate throughout the genome, resulting in transcription of the viral transactivator Tat. The late phase of transcription occurs when enough Tat protein has accumulated. Tat binds to TAR, recruits the pTEFb complex, and causes the hyperphosphorylation of RNA polymerase II, dramatically increasing its ability to elongate.

To understand how postintegration latency is established and to test novel therapeutic approaches for the reactivation of these viral reservoirs, an in vitro cell system reflecting the state of HIV-1 latency is required. Several HIV latently infected cell lines harbor defective proviruses, raising significant questions about their significance in understanding the mechanism of latency in vivo. The latent cell lines ACH2 (T cell) and U1 (promonocytic) contain HIV proviruses that harbor mutations in their Tat-TAR transcriptional axis. Another chronically infected cell line, J-delta-k (T-cell), harbors an HIV-1 provirus lacking NF-κB binding sites in the HIV promoter. These observations suggest that inhibition of transcription is critical to establishment and maintenance of latency.

There is a need in the art for an in vitro cell system that accurately reflects latent immunodeficiency virus infection in vivo. The present invention addresses this need.

Literature

Kulkosky et al. (2001) *Blood* 98:3006-3015; Emiliani et al. (1996) *Proc. Natl. Acad. Sci. USA* 93:6377-6381; Emiliani et al. (1998) *J. Virol.* 72:1666-1670; Antoni et al. (1994) *Virol.* 202:684-694; Carteau et al. (1998) *J. Virol.* 72:4005-4014; U.S. Pat. Nos. 6,225,048; 6,025,124; 5,459,056; and 5,256,534. See U.S. Pat. No. 6,025,124 for a discussion of U1 cells; see U.S. Pat. No. 5,459,056 for a discussion of ACH-2 cells. See U.S. Pat. No. 5,256,534 for a discussion of OM-10.1 cells.

SUMMARY OF THE INVENTION

The present invention provides isolated cells that comprise, integrated into the genome of the cell, a transcription-competent immunodeficiency virus or a transcription-competent immunodeficiency virus-based retroviral vector. Under basal in vitro culture conditions, the immunodeficiency virus is latent, and the expression of the latent immunodeficiency virus can be reactivated. The invention further provides methods of making a subject cell. The invention further provides screening methods for identifying agents that activate a latent immunodeficiency virus; and screening method for identifying agents that block reactivation of latent immunodeficiency virus expression in response to T cell activation signals. The invention further provides agents identified in the subject screening assays. The invention further provides methods of treating an immunodeficiency virus infection.

FEATURES OF THE INVENTION

The present invention features an isolated cell that comprises, integrated into the genome of the cell, a recombinant transcription-competent immunodeficiency virus or virus-based vector, wherein, under basal in vitro culture conditions, the immunodeficiency virus is latent, and wherein expression of the latent immunodeficiency virus can be reactivated. In many embodiments, the isolated cell is an immortalized cell line. In some embodiments, the isolated cell is a T lymphoid cell.

In many embodiments, the immunodeficiency virus is human immunodeficiency virus (HIV), e.g., HIV-1.

The invention further features a method of making an immortalized cell that comprises, integrated into the genome of the cell, a recombinant, transcription-competent recombinant human immunodeficiency virus (HIV), wherein, under basal in vitro culture conditions, the HIV is latent, and wherein expression of the latent HIV can be reactivated. The method generally involves introducing into population of immortalized cells in vitro a recombinant, transcription-competent HIV that comprises a nucleotide sequence encoding a selectable marker operably linked to a promoter; and selecting a cell population that comprises the recombinant HIV integrated into the genome of the cell, and that does not produce the detectable marker. In many embodiments, the method further comprises cloning a cell from the selected cell population. In many embodiments, the selection step results in a first selected cell population, and the method further comprises the steps of contacting the first selected cell population with an agent that activates HIV transcription; and selecting a second population of cells from the first selected population, which second selected population produces the selectable marker. Activating agents include, e.g., an activator of NF-κB, an agent that cross-links cell-surface T-cell receptor, and an inhibitor of histone deacetylase. Non-limiting examples of activating agents are phytohemagglutinin, tetradecanoyl phorbol acetate, TNFα, an anti-CD3 antibody, and trichostatin A.

The invention further features an isolated immortalized cell that comprises, integrated into the genome of the cell, a recombinant transcription-competent human immunodeficiency virus (HIV) that comprises a nucleotide sequence encoding a selectable marker operably linked to a promoter, wherein, under basal in vitro culture conditions, the HIV is latent, and wherein expression of the latent HIV can be reactivated.

The invention further features a method of identifying an agent that activates a latent human immunodeficiency virus (HIV). The method generally involves contacting a cell with a test agent, which cell is an isolated immortalized cell that comprises, integrated into the genome of the cell, a recombinant transcription-competent human immunodeficiency virus (HIV) that comprises a nucleotide sequence encoding a selectable marker operably linked to a promoter, wherein, under basal in vitro culture conditions, the HIV is latent, and wherein expression of the latent HIV can be reactivated; and determining the effect, if any, of the test agent on production of the detectable marker, wherein production of the detectable marker indicates that the test agent activates a latent HIV. In many embodiments, the detectable marker is a fluorescent protein, and the determining step is detection of fluorescence.

The invention further features an active agent that reactivates latent immunodeficiency virus, which agent is identified by a screening method of the invention, and compositions comprising the active agent. In many embodiments, the active agent is formulated in a composition with a pharmaceutically acceptable excipient.

The invention further features a method of reducing the number of cells containing a latent human immunodeficiency virus in an individual. The method generally involves administering to the individual an effective amount of a composition comprising a subject active agent. Generally, the active agent is administered as part of a combination therapy with an anti-HIV therapeutic agent.

The invention further features a method of treating a human immunodeficiency virus infection in an individual. The method generally involves administering to an individual an effective amount of a composition comprising a subject active agent; and administering to the individual an effective amount of an agent that inhibits an immunodeficiency virus function selected from the group consisting of viral replication, viral protease activity, viral reverse transcriptase activity, viral entry into a cell, viral integrase activity, viral Rev activity, viral Tat activity, viral Nef activity, viral Vpr activity, viral Vpu activity, and viral Vif activity.

BRIEF DESCRIPTION OF THE DRAWINGS

FIGS. 1A-C depict enrichment and purification of HIV-latently infected cells by FACS.

FIGS. 2A-C depict characterization of latently infected clones.

FIGS. 3A-D depict data showing that latency is associated with preferred integration in or near alphoid repeats.

FIG. 6 depicts the nucleotide sequences at the integration site of provirus integrated into alphoid repeats from PBMCs from HIV-1-infected individuals treated with highly active antiretroviral therapy.

DEFINITIONS

Figure 1A:
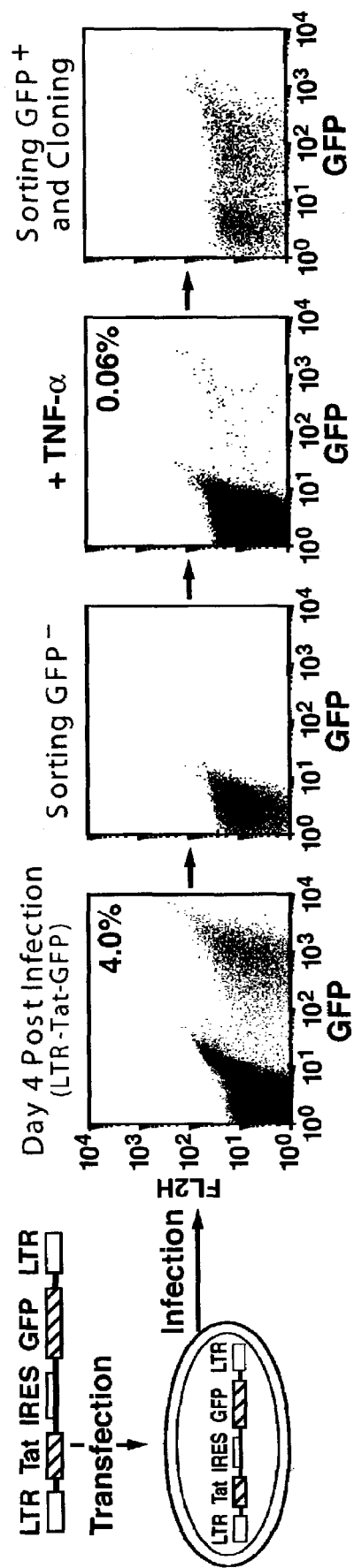

As used herein, the terms "treatment", "treating", and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment", as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease. In the context of immunodeficiency virus infection, the term "treatment" encompasses prevention of establishment of a systemic infection following initial contact with the virus; and prophylactic treatment of an individual not yet infected with the virus.

The terms "individual," "host," "subject," and "patient," used interchangeably herein, refer to a mammal, including, but not limited to, murines, felines, simians, humans, mammalian farm animals, mammalian sport animals, and mammalian pets. The term includes mammals that are susceptible to infection by an immunodeficiency virus.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as CD4$^+$ T lymphocytes, glial cells, macrophages, tumor cells, peripheral blood mononuclear cells (PBMC), and the like. The term "biological sample" encompasses a clinical sample, and also includes cells in culture, cell supernatants, tissue samples, organs, bone marrow, and the like.

The term "immunodeficiency virus" as used herein, refers to human immunodeficiency virus-1 (HIV-1); human immunodeficiency virus-2 (HIV-2); any of a variety of HIV subtypes and quasispecies; simian immunodeficiency virus (SIV); and feline immunodeficiency virus (FIV). As used herein in the context of latent immunodeficiency virus in a subject isolated cell, the term also includes immunodeficiency virus-based retroviral vectors (e.g., recombinant immunodeficiency virus).

The term "transcription competent" as used herein in the context of transcription-competent latent immunodeficiency virus, refers to a latent immunodeficiency virus (including latent immunodeficiency virus-based retroviral vectors) that encodes functional Tat and has a functional TAR site in the LTR.

The term "latent," as used herein in the context of a latent immunodeficiency virus refers to a genomically integrated immunodeficiency virus (including a latent immunodeficiency virus-based retroviral vector, e.g., a recombinant immunodeficiency virus) that is transcriptionally silent, e.g., immunodeficiency virus transcripts are undetectable or are at background levels, in a cell comprising the latent immunodeficiency virus.

The term "reactivated," as used herein in the context of in vivo reactivated immunodeficiency virus, refers to an immunodeficiency virus that, after a period of latency, becomes transcriptionally active, and in many instances forms infectious viral particles. The term "reactivated," as used herein in the context of in vitro reactivated immunodeficiency virus in a subject cell, refers to an immunodeficiency virus (e.g., a recombinant immunodeficiency virus) that, after a period of latency, becomes transcriptionally active, i.e., a functional Tat protein mediates transcription from a functional immunodeficiency virus promoter (e.g., a long terminal repeat promoter). In those embodiments in which a reactivated recombinant immunodeficiency virus is not replication competent, the recombinant immunodeficiency virus can be packaged into infectious particles by providing any missing viral proteins (e.g., gag and env proteins) via a helper virus.

As used herein the term "isolated," in the context of a subject isolated cell, refers to a cell that is in an environment different from that in which the cell naturally occurs. As used herein, the term "clonal cell line" refers to a cloned cell line that is typically immortalized, e.g., under suitable in vitro culture conditions, the cell line divides virtually indefinitely. Isolated cells are also referred to herein as "host cells."

The term "host cell" includes an individual cell or cell culture which can be or has been a recipient of any recombinant vector(s) or construct of the invention. Host cells include progeny of a single host cell, and the progeny may not necessarily be completely identical (in morphology or in total DNA complement) to the original parent cell due to natural, accidental, or deliberate mutation and/or change. A host cell includes cells tranfected or infected in vitro with a recombinant vector or a construct of the invention. A host cell which comprises a recombinant vector or construct of the invention is a "recombinant host cell."

"Alkyl" is a monovalent, saturated or unsaturated, straight, branched or cyclic, aliphatic (i.e., not aromatic) hydrocarbon group. In various embodiments, the alkyl group has 1-20 carbon atoms, i.e., is a C1-C20 (or $C_1$-$C_{20}$) group, or is a C1-C18 group, a C1-C12 group, a C1-C6 group, or a C1-C4 group. Independently, in various embodiments, the alkyl group: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than three triple bonds); is, or includes, a cyclic structure; is acyclic. Exemplary alkyl groups include $C_1$alkyl (i.e., —$CH_3$ (methyl)), $C_2$alkyl (i.e., —$CH_2CH_3$ (ethyl), —CH=$CH_2$ (ethenyl) and —C≡CH (ethynyl)) and $C_3$alkyl (i.e., —$CH_2CH_2CH_3$ (n-propyl), —$CH(CH_3)_2$ (i-propyl), —CH=CH—$CH_3$ (1-propenyl), —C≡C—$CH_3$ (1-propynyl), —$CH_2$—CH=$CH_2$ (2-propenyl), —$CH_2$—C≡CH (2-propynyl), —$C(CH_3)$=$CH_2$ (1-methylethenyl), and —$CH(CH_2)_2$ (cyclopropyl)).

"Ar" indicates a carbocyclic aryl group selected from phenyl, substituted phenyl, naphthyl, and substituted naphthyl. Suitable substituents on a phenyl or naphthyl ring include $C_1$-$C_6$alkyl, $C_1$-$C_6$alkoxy, carboxyl, carbonyl($C_1$-$C_6$)alkoxy, halogen, hydroxyl, nitro, —$SO_3H$, and amino.

"Aryl" is a monovalent, aromatic, hydrocarbon, ring system. The ring system may be monocyclic or fused polycyclic (e.g., bicyclic, tricyclic, etc.). In various embodiments, the monocyclic aryl ring is C5-C10, or C5-C7, or C5-C6, where these carbon numbers refer to the number of carbon atoms that form the ring system. A C6 ring system, i.e., a phenyl ring, is a preferred aryl group. In various embodiments, the polycyclic ring is a bicyclic aryl group, where preferred bicyclic aryl groups are C8-C12, or C9-C10.

"Arylene" is a polyvalent, aromatic hydrocarbon, ring system. The ring system may be monocyclic or fused polycyclic (e.g., bicyclic, tricyclic, etc.). In some embodiments, the monocyclic arylene group is C5-C10, or C5-C7, or C5-C6, where these carbon numbers refer to the number of carbon atoms that form the ring system. A C6 ring system, i.e., a phenylene ring, is an exemplary aryl group. In some embodiments, the polycyclic ring is a bicyclic arylene group, where exemplary bicyclic arylene groups are C8-C12, or C9-C10. The arylene group may be divalent, i.e., it has two open sites that each bond to another group; or trivalent, i.e., it has three open sites that each bond to another group; or it may have more than three open sites.

"Carbocycle" refers to a ring formed exclusively from carbon, which may be saturated or unsaturated, including aromatic. The ring may be monocyclic (e.g., cyclohexyl, phenyl), bicyclic (e.g., norbornyl), polycyclic (e.g., adamantyl) or contain a fused ring system (e.g., decalinyl, naphthyl). In one embodiment, the ring is monocyclic and formed from 5, 6 or 7 carbons. In one embodiment, the ring is bicyclic and formed from 7, 8 or 9 carbons. In one embodiment, the ring is polycyclic and formed from 9, 10 or 11 carbons. In one embodiment, the ring includes a fused ring system and is formed from 8-12 carbons. Thus, in one embodiment, the carbocycle is formed from 5-12 ring carbons.

"Heteroalkyl" is an alkyl group (as defined herein) wherein at least one of the carbon atoms is replaced with a heteroatom. Exemplary heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted. As another example, trifluoromethyl is a heteroalkyl group wherein the three methyl groups of a t-butyl group are replaced by fluorine.

"Heteroalkylene" is an alkylene group (as defined herein) wherein at least one of the carbon atoms is replaced with a heteroatom. Exemplary heteroatoms are nitrogen, oxygen, sulfur, and halogen. A heteroatom may, but typically does not, have the same number of valence sites as carbon. Accordingly, when a carbon is replaced with a heteroatom, the number of hydrogens bonded to the heteroatom may need to be increased or decreased to match the number of valence sites of the heteroatom, as explained elsewhere herein.

"Heteroaryl" is a monovalent aromatic ring system containing carbon and at least one heteroatom in the ring. The heteroaryl group may, in various embodiments, have one heteroatom, or 1-2 heteroatoms, or 1-3 heteroatoms, or 1-4 heteroatoms in the ring. Heteroaryl rings may be monocyclic or polycyclic, where the polycyclic ring may contained fused, spiro or bridged ring junctions. In one embodiment, the heteroaryl is selected from monocyclic and bicyclic. Monocyclic heteroaryl rings may contain from about 5 to about 10 member atoms (carbon and heteroatoms), e.g., from 5-7, and most often from 5-6 member atoms in the ring. Bicyclic heteroaryl rings may contain from about 8-12 member atoms, or 9-10 member atoms in the ring. The heteroaryl ring may be unsubstituted or substituted. In one embodiment, the heteroaryl ring is unsubstituted. In another embodiment, the heteroaryl ring is substituted. Exemplary heteroaryl groups include benzofuran, benzothiophene, furan, imidazole, indole, isothiazole, oxazole, piperazine, pyrazine, pyrazole, pyridazine, pyridine, pyrimidine, pyrrole, quinoline, thiazole and thiophene.

"Heteroarylene" is a polyvalent aromatic ring system containing carbon and at least one heteroatom in the ring. In other words, a heteroarylene group is a heteroaryl group that has more than one open site for bonding to other groups. The heteroarylene group may, in various embodiments, have one heteroatom, or 1-2 heteroatoms, or 1-3 heteroatoms, or 1-4 heteroatoms in the ring. Heteroarylene rings may be monocyclic or polycyclic, where the polycyclic ring may contained fused, spiro or bridged ring junctions. In one embodiment, the heteroaryl is selected from monocyclic and bicyclic. Monocyclic heteroarylene rings may contain from about 5 to about 10 member atoms (carbon and heteroatoms), preferably from 5-7, and most preferably from 5-6 member atoms in the ring. Bicyclic heteroarylene rings may contain from about 8-12 member atoms, or 9-10 member atoms in the ring.

"Heteroatom" is a halogen, nitrogen, oxygen, silicon or sulfur atom. Groups containing more than one heteroatom may contain different heteroatoms.

"Heterocycle" refers to a ring containing at least one carbon and at least one heteroatom. The ring may be monocyclic (e.g., morpholinyl, pyridyl), bicyclic (e.g., bicyclo[2.2.2]octyl with a nitrogen at one bridgehead position), polycyclic, or contain a fused ring system. In one embodiment, the ring is monocyclic and formed from 5, 6 or 7 atoms. In one embodiment, the ring is bicyclic and formed from 7, 8 or 9 atoms. In one embodiment, the ring is polycyclic and formed from 9, 10 or 11 atoms. In one embodiment, the ring includes a fused ring system and is formed from 8-12 atoms. Thus, in one embodiment, the heterocycle is formed from 5-12 ring atoms. In one embodiment, the heteroatom is selected from oxygen, nitrogen and sulfur. In one embodiment, the heterocycle contains 1, 2 or 3 heteroatoms.

"Pharmaceutically acceptable salt" and "salts thereof" in the compounds of the resent invention refers to acid addition salts and base addition salts.

Acid addition salts refer to those salts formed from compounds of the present invention and inorganic acids such as hydrochloric acid, hydrobromic acid, sulfuric acid, nitric acid, phosphoric acid and the like, and/or organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

Base addition salts refer to those salts formed from compounds of the present invention and inorganic bases such as sodium, potassium, lithium, ammonium, calcium, magnesium, iron, zinc, copper, manganese, aluminum salts and the like. Suitable salts include the ammonium, potassium, sodium, calcium and magnesium salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, trimethamine, dicyclohexylamine, lysine, arginine, histidine, caffeine, procaines, hydrabamine, choline, betaine, ethylenediamine, glucosamine, methylglucamine, theobromine, purines, piperazine, piperidine, N-ethylpiperidine, and the like.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a cell" includes a plurality of such cells and reference to "the agent" includes reference to one or more agents and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides an isolated cell that comprises, integrated into the genome of the cell, a transcription-competent immunodeficiency virus or a transcription-competent immunodeficiency virus-based retroviral vector. Under basal in vitro culture conditions, the immunodeficiency virus is latent, and the expression of the latent immunodeficiency virus can be reactivated. The latent immunodeficiency virus is transcriptionally inactive, but is fully transcriptionally competent. Previously available cell lines such as ACH2, U1, A2.01, and derivatives of such cell lines, contain latent HIV that is not transcriptionally competent. The latent HIV in such cell lines contains mutations in Tat and/or in the LTR, e.g., in the TAR region or the NFκB binding site. Therefore, the previously available cell lines are not representative of the cells in a reservoir of latently infected cells in an infected individual. The isolated cells of the instant invention are transcriptionally competent, e.g., the Tat protein is functional, and the viral LTR is functional (e.g., has functional TAR and other elements necessary for transcriptional activation. Thus, the subject cells are representative of cells in a reservoir of latently infected cells in an infected individual.

The subject cells are useful in screening methods for identifying agents that activate latent immunodeficiency virus. Agents that activate latent immunodeficiency virus are useful, particularly in combination with established anti-HIV therapeutic agents, to reduce the reservoir of latently infected cells in an HIV-infected individual. Such agents are useful to reduce or eliminate the problem of reemergence of viremia following cessation or interruption of treatment with anti-HIV therapeutic agent(s), and therefore render existing therapeutic agents more effective.

The subject cells are also useful in screening methods for identifying agents that block or reduce reactivation of latent immunodeficiency virus transcription in response to T cell activation signals. Such agents are useful to suppress reactivation of a latent immunodeficiency virus.

The invention further provides methods of making a subject cell (e.g., a cell that harbors a latent, transcription competent immunodeficiency virus). The invention further provides screening methods for identifying agents that activate a latent immunodeficiency virus; and screening methods for identifying agents that suppress or block activation of a latent immunodeficiency virus. The invention further provides agents identified using a screening method of the invention. The invention further provides methods of treating an HIV infection, with the-goal of eradicating the HIV from the infected individual (in contrast to suppressing the infection, as is achieved using currently applied anti-HIV therapy).

Isolated Cells with Latent Immunodeficiency Virus

The present invention provides an isolated cell that comprises, integrated into the genome of the cell, a transcription-competent immunodeficiency virus or a transcription-competent immunodeficiency virus-based retroviral vector. While human immunodeficiency virus (HIV) is exemplified in this specification, the disclosure pertains to other immunodeficiency viruses as well and is not meant to be limited to HIV.

Under basal in vitro culture conditions, the genomically integrated HIV is latent, and the expression of the latent HIV can be reactivated. The subject cells are useful as in vitro models for a latent HIV infection in vivo and for screening for agents that activate latent HIV.

The latent HIV is transcriptionally inactive under basal in vitro culture conditions, but is fully transcriptionally competent. "Basal in vitro culture conditions" typically involve standard culture media, a temperature of about 37° C., and 5% $CO_2$. Standard culture media include, but are not limited to, RPMI 1640 medium, McCoy's 5A medium, Leibovitz's L15 medium, Eagle's minimal essential medium, Dulbecco's modified Eagle's medium, and the like. In many cases, the medium will be supplemented with additional components, e.g., 10 mM HEPES buffer; 2 mM L-glutamine; 100 U/ml penicillin; 100 µg/ml streptomycin; and heat-inactivated fetal calf serum, in an amount (in volume/volume) of from about 5% to about 10%, from about 10% to about 15%, or from about 15% to about 20%, or higher.

Basal in vitro culture conditions generally exclude the presence in the medium of a factor(s) that would activate HIV transcription and/or production of HIV virions, including the factors listed below for reactivation of latent HIV.

Under certain cell culture conditions, the latent HIV can be reactivated, e.g., the latent HIV becomes transcriptionally activated. In many embodiments, reactivation of the latent virus (or recombinant virus) does not require a host cell factor). Culture conditions that result in reactivation of latent HIV include contacting the cell for a suitable period of time with an effective amount of one or more reactivating agents. Agents that reactivate latent HIV in a subject cell are termed "reactivating agents" and include, but are not limited to, activators of NF-κB, including, but not limited to, phytohemagglutinin (PHA), phorbol esters, e.g., tetradecanoyl phorbol acetate (TPA), and TNFα; exposure to an antigen for which a cell surface T-cell receptor is specific; an agent that cross-links cell-surface T-cell receptor, e.g., anti-CD3 antibody; inhibitors of histone deacetylase, e.g., trichostatin A, sodium butyrate, and trapoxin.

An effective amount of a reactivating agent is an amount effective to achieve transcriptional activation of the latent immunodeficiency virus. Whether transcription is reactivated can be determined using any known method, including, but not limited to, detecting production of a detectable marker operably linked to an HIV promoter; and detecting production of a viral protein under transcriptional control of an HIV promoter. Detection of a detectable marker is carried out using a method suitable to the particular marker. For example, where the marker is a fluorescent protein, fluorescence is detected; where the marker is a luminescent protein, luminescence is detected; and the like. Such methods are well known to those skilled in the art.

Effective amounts of exemplary reactivating agents are as follows: from about 5 nM to about 10 nM TPA; from about 5 ng/ml to about 20 ng/ml TNF-α; from about 2.5 µg/ml to about 10 µg/ml PHA; from about 2.5 µg/ml to about 10 µg/ml anti-CD3 antibody; and from about 200 nM to about 800 nM TSA. Non-limiting examples of effective amounts of exemplary reactivating agents are as follows: 10 nM TPA; 10 ng/ml TNF-α; 5 µg/ml PHA; 5 µg/ml anti-CD3 antibody; and 400 nM TSA.

Suitable periods of time for contacting a cell with a reactivating agent are from about 0.5 hour to about 24 hours, e.g., from about 1 hour to about 2 hours, from about 2 hours to about 4 hours, from about 4 hours to about 8 hours, from about 8 hours to about 12 hours, from about 12 hours to about 16 hours, from about 16 hours to about 20 hours, or from about 20 hours to about 24 hours. Contacting a cell with an effective amount of a reactivating agent is typically conducted under standard culture conditions of 37° C. and 5% $CO_2$.

The latent immunodeficiency virus (or latent immunodeficiency virus-based retroviral vector in the subject isolated cells is transcription competent, and includes a fully functional transactivator protein (Tat) and transcriptional activation response region (TAR). The TAR, which is part of the long terminal repeat (LTR), is bound by Tat protein during transcription activation. In many embodiments, the encoded Tat protein and the TAR are wild-type. In other embodiments, the encoded Tat protein and/or the TAR include one or more amino acid or nucleotide sequence changes compared to the wild-type, but remain fully functional, e.g., Tat binds to TAR, and Tat-dependent transcription occurs when the subject cell is contacted with an activating agent.

In many embodiments, the latent transcription-competent immunodeficiency virus (or latent transcription-competent immunodeficiency virus-based retroviral vector) is not replication competent. In many of these embodiments, a portion or the entire nucleotide sequence that encodes the envelope protein in the native immunodeficiency virus is deleted (e.g., not included in the vector), and the immunodeficiency virus cannot be packaged without a helper virus vector. Vectors that do not encode an immunodeficiency virus envelope protein are used in many embodiments because of the ease of cloning and elimination of toxicity associated with the envelope protein. In these embodiments, the latent transcription-competent immunodeficiency virus (or latent transcription-competent immunodeficiency virus-based retroviral vector) does not form infectious virions when reactivated.

Where the immunodeficiency virus is recombinant and is not replication competent, viral particles are generated using a helper virus which provides the viral proteins that are not encoded by the recombinant immunodeficiency virus. Those skilled in the art are familiar with helper virus constructs and packaging cell lines that are used to package viral constructs (recombinant virus) that lacks coding sequences for one or more viral proteins, e.g., gag and env, that are required for packaging.

In some embodiments, the latent immunodeficiency virus in the subject cells is replication competent, e.g., the latent immunodeficiency virus, when reactivated, is transcribed, viral proteins are translated, and the resultant viral genome can replicate in a permissive cell. Whether the latent immunodeficiency virus is replication competent can be determined using known methods.

In some embodiments, the latent immunodeficiency virus in the subject cells forms infectious virions when reactivated, e.g., the latent immunodeficiency virus, when reactivated, is transcribed, viral proteins are translated, and infectious virions are formed. Whether the latent immunodeficiency virus forms infectious virus when reactivated can be determined by reactivating the latent immunodeficiency virus, as described above, and determining infectivity of culture supernatant on permissive cells. Any known method can be used. As one non-limiting example, a subject cell containing a latent HIV is reactivated as described above, and culture supernatant collected. The presence and/or number of infectious particles are determined by infecting Jurkat cells with the culture supernatant.

In many embodiments, the latent immunodeficiency virus is integrated in the genome at or near an alphoid repeat (e.g., adjacent to, or within an alphoid repeat, or within from about 10 base pairs (bp) to about 50 bp, from about 50 bp to about 100 bp, from about 100 bp to about 500 bp, from about 500 bp to about 1 kilobase pairs (kb), from about 1 kb to about 5 kb, or from about 5 kb to about 10 kb of an alphoid repeat). Alphoid repeats are approximately 171 base-pair repeats and are the smallest subunit of the alpha satellite, the major component of centromeres. Alphoid repeats are known in the art and the sequences of numerous centromeric alphoid repeats are publicly available, e.g., GenBank Accession Nos. AF153368; D29750; X03113; X03115; X66291; and M16101.

Cells

Any of a variety of cell can comprise a transcription-competent immunodeficiency virus integrated into the genome of the cell. In some embodiments, the cell is an immortalized cell. In other embodiments, the cell is a primary cell culture and is not immortalized. In general, the cell is a T cell or a T cell line. In many embodiments, the cell is a T cell or an immortalized T cell line that is permissive for an immunodeficiency virus, e.g., can be infected by an immunodeficiency virus, e.g., the T cell or immortalized T cell line expresses on its cell surface a CD4 receptor and a co-receptor (e.g., CXCR4 or CCR5).

Suitable immortalized T cell lines include, but are not limited to, Jurkat; MOLT-16; MOLT-17; MOLT-3; MOLT-4, Karpas-299; HuT78; HSB-2; CCRF-CEM; SupT1; H9; and the like. Such cell lines are publicly available, e.g., from the American Type Culture Collection.

Primary cultures of T cells can be obtained using standard methods. For example, human peripheral blood mononuclear cells (PBMC) are removed from a human donor, and the T lymphocytes are separated from other lymphoid cells by any known method, including, but not limited to Ficoll-Hypaque cell separation. The cells can then be further subjected to cell sorting on the basis of cell surface expression of CD4 and CD3 molecules, e.g., using a fluorescence activated cell sorter and labeled antibody specific for CD4 and for CD3. The cells are then stimulated in the presence of PHA and grown continuously in the presence of low concentrations of recombinant IL-2, according to standard protocols.

In some embodiments, a subject isolated cell is an isolated clonal cell line. In some embodiments, a subject isolated cell is a member of a homogeneous population of cells (e.g., a population of cloned cells from a single cloned cell line). The immunodeficiency virus need not be integrated at the same genomic site in each cell of a population, and to that extent, the population can be considered heterogeneous, even though the cells used to make the population are from a single cell line.

Immunodeficiency Virus and Vectors

The latent immunodeficiency virus in the subject isolated cells is transcription competentt. The latent immunodeficiency virus can be wild-type or recombinant. In many embodiments, the latent immunodeficiency virus is recombinant. Recombinant immunodeficiency virus is also referred to as "immunodeficiency virus-derived vector," "immunodeficiency virus-based vector," or "immunodeficiency virus-based retroviral vector." In many embodiments, the recombinant immunodeficiency virus-based vector is generated using standard recombinant DNA methods, and comprises a detectable marker for viral expression (transcription).

In some embodiments, the latent immunodeficiency virus is a wild-type immunodeficiency virus. HIV genome sequences are known in the art for a variety of HIV-1 and HIV-2 strains, and can be found in GenBank under various accession numbers, including AJ203647, AAAJ302646; AF133821, NC001802, L36874, and NC001722. SIV genome sequences are known in the art for a variety of SIV strains, and can be found in GenBank under various accession numbers, including AF334679, and NC001549. Any of a variety of strains and quasispecies can be used.

In many embodiments, the transcription-competent immunodeficiency virus is recombinant, e.g., the immunodeficiency virus comprises heterologous (non-immunodeficiency virus) sequences. In many of these embodiments, the recombinant immunodeficiency virus is in a vector. Suitable vectors include, but are not limited to, plasmid vectors; Semliki forest virus vectors; vaccinia virus vectors; adenoviral vectors; and the like. Many such vectors are available commercially. To prepare the constructs, the immunodeficiency polynucleotide is inserted into a vector, typically by means of DNA ligase attachment to a cleaved restriction enzyme site in the vector.

In some embodiments, the recombinant immunodeficiency virus comprises a nucleotide sequence that encodes a detectable marker protein. Suitable detectable marker proteins include, but are not limited to, fluorescent proteins (e.g., a green fluorescent protein (GFP) (including enhanced GFP, e.g., available from Clontech); a fluorescent protein from an Anthozoa species (as described in, e.g., Matz et al. (1999) *Nat. Biotech.* 17:969-973); β-galactosidase; luciferase; and the like. The nucleotide sequence encoding the detectable marker is operably linked to a promoter. In general, the promoter is an immunodeficiency virus promoter, and the detectable marker provides a read-out for transcriptional activity of the immunodeficiency virus.

Recombinant vectors need not include the entire immunodeficiency virus genome. In many embodiments, a recombinant vector includes at least the long terminal repeat (LTR) from the immunodeficiency virus, a nucleotide sequence encoding the Tat protein, and a nucleotide sequence encoding a detectable marker, where both the Tat-encoding sequence and the detectable marker-encoding sequence are operably linked to the viral LTR, e.g., are under transcriptional control of the viral LTR.

The recombinant vector may further include other elements, such as sequences necessary for propagation of the vector, such as an origin of replication for replication in a bacterial of eukaryotic cell; sequences encoding a selectable marker for selection of bacterial cells that contain the vector, such as antibiotic resistance genes (e.g., ampicillin resistance; and the like). Such elements are well known to those skilled in the art.

In one particular embodiment, the recombinant immunodeficiency virus is an HIV-derived vector as described in the Examples and referred to as LTR-Tat-IRES-GFP, where both Tat and GFP coding sequences are under transcriptional control of the HIV long terminal repeat (LTR). Both open reading frames are translated from a single mRNA due to the presence of an internal ribosome entry site (IRES) derived from the encephalomyocarditis virus.

A number of IRES elements are known in the art, and any such IRES can be used in a recombinant immunodeficiency virus-based vector. Naturally occurring IRES sequences are known in the art and include, but are not limited to, IRES sequences derived from mengovirus, bovine viral diarrhea virus (BVDV), hepatitis C virus (HCV; e.g., nucleotides 1202-1812 of the nucleotide sequence provided under GenBank Accession number AJ242654), GTX, Cyr61a, Cyr61b, poliovirus, the immunoglobulin heavy-chain-binding protein (BiP), immunoglobulin heavy chain, a picornavirus, murine encephalomyocarditis virus, poliovirus, and foot and mouth disease virus (e.g., nucleotide numbers 600-1058 of the nucleotide sequence provided under GenBank Accession No. AF308157). Other IRES sequences such as those reported in WO 96/01324; WO 98/49334; WO 00/44896; and U.S. Pat. No. 6,171,821 can be used.

Methods of Generating a Cell with Latent Immunodeficiency Virus

The present invention provides a method of making an isolated cell that comprises, integrated into the genome of the cell, a transcription-competent immunodeficiency virus (or a transcription-competent immunodeficiency virus-based vector), such that under basal in vitro culture conditions, the immunodeficiency virus is latent, and expression of the latent immunodeficiency virus can be reactivated. The method generally involves introducing into a population of cells in vitro a recombinant, transcription-competent immunodeficiency virus (or a transcription-competent immunodeficiency virus-based vector) that comprises a nucleotide sequence encoding a selectable marker operably linked to an immunodeficiency virus LTR promoter; and selecting a cell from the population that comprises the recombinant immunodeficiency virus integrated into the genome of the cell, and that does not produce the detectable marker.

In many embodiments, the method involves infecting a population of cells in vitro with a transcription-competent immunodeficiency virus-based vector that comprises a nucleotide sequence encoding a selectable marker operably linked to an immunodeficiency virus LTR promoter; and selecting a cell from the population that comprises the recombinant immunodeficiency virus integrated into the genome of the cell, and that does not produce the detectable marker.

The recombinant immunodeficiency virus is introduced into cells using any known means, including, but not limited to, electroporation, calcium phosphate precipitation, infection (where the recombinant immunodeficiency virus is packaged into a viral particle), and the like.

The recombinant immunodeficiency virus is contacted with the cell population at a low multiplicity of infection (MOI) to reduce the likelihood that more than one recombinant virus enters a given cell. A suitable MOI is from about 0.01 to about 0.05, or from about 0.05 to about 0.1.

In many embodiments, the detectable marker is a fluorescent protein, and detection of the marker is by flow cytometry, using a fluorescence activated cell sorter (FACS). In many embodiments, the selection step involves selecting a population of cells that, under basal in vitro culture conditions, does not fluoresce or that has low fluorescence, such that the relative fluorescence units are from $10^0$ to about $10^1$. This first selected population includes both uninfected cells and cells that are have latent HIV.

In general, the first selected population is subjected to at least one additional selection. A second selection is achieved by contacting the first selected population for a suitable period of time with an agent that reactivates the latent HIV. When the first selected population is contacted with an agent that reactivates the latent HIV, a proportion of the first selected population will exhibit no or low levels of detectable marker, and a proportion will exhibit higher levels of detectable marker. In this second selection step, cells that exhibit fluorescence in a range of from about $10^2$ to about $10^3$ or higher, relative fluorescence units are selected, and are a second selected population of cells. The second selected population of cells may then be subjected to a third selection step.

A third selection step involves maintaining the second selected population for a suitable period of time under basal in vitro culture conditions, and selecting a population that exhibits no or low fluorescence such that the relative fluorescence units are from $10^0$ to about $10^1$, which population is a third selected population.

Any of the first, second, or third selected populations is subjected to cloning, e.g., limiting dilution cloning. Cells are plated in individual wells of a multi-well plate at a density of one cell per well.

Screening Methods

The present invention further provides screening methods for identifying an agent that activates a latent immunodeficiency virus. The methods generally involve contacting a subject cell that comprises a transcription-competent latent immunodeficiency virus (or a transcription-competent recombinant immunodeficiency virus-based vector) integrated into the genome of the cell with a test agent; and determining whether the latent immunodeficiency virus is activated.

The present invention further provides screening methods for identifying an agent that blocks reactivation of latent immunodeficiency virus in response to a T cell activation signal. The methods generally involve contacting a subject cell that comprises a transcription-competent latent immunodeficiency virus (or a transcription-competent recombinant immunodeficiency virus-based vector) integrated into the genome of the cell with a test agent and an agent that activates T cells; and determining whether the latent immunodeficiency virus is activated.

The terms "candidate agent," "agent", "substance," "test agent," and "compound" are used interchangeably herein. Candidate agents encompass numerous chemical classes, and are generally synthetic, semi-synthetic, or naturally occurring inorganic or organic molecules. Candidate agents may be small organic compounds having a molecular weight of more than 50 and less than about 2,500 daltons. Candidate agents may comprise functional groups necessary for structural interaction with proteins, particularly hydrogen bonding, and may include at least an amine, carbonyl, hydroxyl or carboxyl group, and may contain at least two of the functional chemical groups. The candidate agents may comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

A candidate agent is assessed for any cytotoxic activity it may exhibit toward control cells not infected with an immunodeficiency virus, using well-known assays, such as trypan blue dye exclusion, an MTT ([3-(4,5-dimethylthiazol-2-yl)-2,5-diphenyl-2 H-tetrazolium bromide]) assay, and the like. Agents that do not exhibit cytotoxic activity toward control cells not infected with an immunodeficiency virus are considered suitable candidate agents.

Assays of the invention usually include one or more controls. Thus, a test sample includes a test agent, and a control sample has all the components of the test sample except for the test agent.

A variety of reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as nuclease inhibitors, anti-microbial agents, etc. may be used. The components may be added in any order. Incubations are performed at any suitable temperature, typically between 37° C. and 40° C. Incubation periods are selected for optimum activity, but may also be optimized to facilitate rapid high-throughput screening. Typically between 0.1 and 1 hour will be sufficient.

In some embodiments, the subject method of identifying an agent that activates a latent human immunodeficiency virus involves contacting a subject cell with a test agent, which cell comprises a recombinant, genomically-integrated, latent, transcription-competent HIV that comprises a nucleotide sequence encoding a selectable marker operably linked to an HIV promoter (as described above); and determining the effect, if any, of the test agent on production of the detectable marker, wherein production of the detectable marker indicates that the test agent activates a latent HIV.

In other embodiments, the subject method for identifying an agent that blocks reactivation of latent immunodeficiency virus in response to a T cell activation signal involves contacting a subject cell with a test agent and a reactivating agent, which subject cell comprises a recombinant genomically-integrated, latent, transcription-competent HIV that comprises a nucleotide sequence encoding a selectable marker operably linked to an HIV promoter; and determining whether the latent immunodeficiency virus is activated. A decrease in production of the detectable marker, compared to a control lacking the test agent, indicates that the test agent blocks activation of the latent HIV. Suitable reactivating agent include those described above.

Active Agents

The invention further provides an agent that activates a latent immunodeficiency virus in a cell; and an agent that blocks reactivation of latent immunodeficiency virus. In many embodiments, the agent is identified using a screening method of the invention.

In general, the agent is one that is biocompatible, e.g., that does not exhibit any untoward effects toward cells not infected with an immunodeficiency virus, where untoward effects include cytotoxicity, induction of inflammation, induction of cell proliferation, and the like.

In some embodiments, an active agent has a structure represented by the generic formula #1 as set forth below:

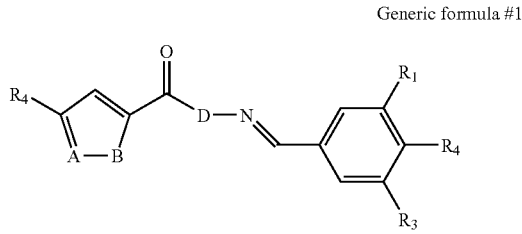

Generic formula #1 and stereoisomers, solvates, and pharmaceutically acceptable salts thereof, and a pharmaceutically acceptable carrier, diluent or excipient, where:

each of $R_1$, $R_2$, and $R_3$ is independently selected from direct bond, H, hydryoxyl, aryl, alkyl, cycloalkyl, and —$NH_2$; $R_4$ is H, —OH, alkyl, aryl and heteroaryl; A is C or N; and each of B and D is independently $CH_2$ or NH.

In generic formula #1, in some embodiments, each of $R_1$, $R_2$, and $R_3$ is independently selected from alkyl, aryl and heteroaryl, wherein each of alkyl, aryl and heteroaryl may be substituted with one or more groups selected from $C_1$-$C_{20}$alkyl, $C_6$-$C_{10}$aryl, heteroalkyl and heteroaryl. In some embodiments, each of $R_1$, $R_2$, and $R_3$ is independently selected —O—$CH_3$ and —OH.

In generic formula #1, $R_4$ is H, —OH, alkyl, aryl and heteroaryl. In some embodiments, $R_4$ is a single substituted or unsubstituted aryl group or multiple substituted or unsubstituted aryl groups.

In other embodiments, an active agent has a structure represented by the generic formula #2 as set forth below,

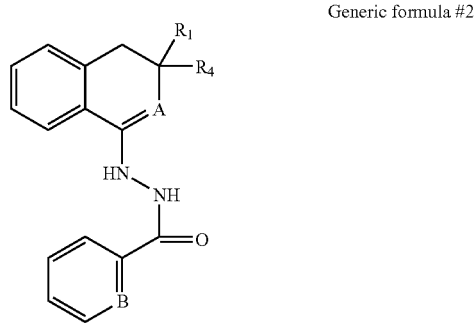

Generic formula #2 and stereoisomers, solvates, and pharmaceutically acceptable salts thereof, and a pharmaceutically acceptable carrier, diluent or excipient, where:

each of $R_1$ and $R_2$ is independently selected from direct bond, H, hydryoxyl, aryl, alkyl, cycloalkyl, and —$NH_2$; and each of A and B is independently N or CH.

In other embodiments, an active agent has a structure represented by the generic formula #3 as set forth below,

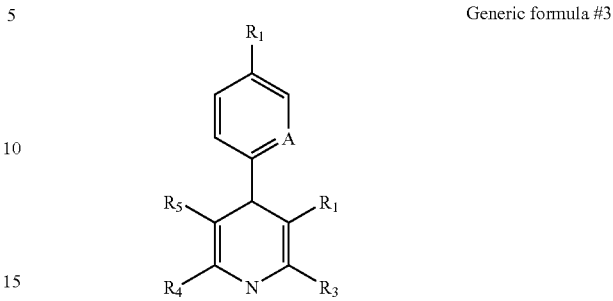

Generic formula #3 and stereoisomers, solvates, and pharmaceutically acceptable salts thereof, and a pharmaceutically acceptable carrier, diluent or excipient, where each of $R_1$, $R_2$, $R_3$, $R_4$, and $R_5$ is independently selected from direct bond, H, hydryoxyl, aryl, alkyl, cycloalkyl, and —$NH_2$. In some embodiments, each of $R_1$, $R_2$, $R_3$, and $R_4$ is independently selected from alkyl, aryl and heteroaryl, wherein each of alkyl, aryl and heteroaryl may be substituted with one or more groups selected from $C_1$-$C_{20}$alkyl, $C_6$-$C_{10}$aryl, heteroalkyl and heteroaryl.

In particular embodiments, an active agent is an agent having any one of the structures depicted in Example 2, and stereoisomers, solvates, and pharmaceutically acceptable salts thereof, and a pharmaceutically acceptable carrier, diluent or excipient.

Formulations

In general, a subject agent is prepared in a pharmaceutically acceptable composition for delivery to a host.

Pharmaceutically acceptable carriers preferred for use with a subject agent may include sterile aqueous of non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, and microparticles, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like. A composition comprising a subject agent may also be lyophilized using means well known in the art, for subsequent constitution and use according to the invention.

In general, the pharmaceutical compositions can be prepared in various forms, such as granules, tablets, pills, suppositories, capsules, suspensions, salves, lotions and the like. Pharmaceutical grade organic or inorganic carriers and/or diluents suitable for oral and topical use can be used to make up compositions comprising the therapeutically-active compounds. Diluents known to the art include aqueous media, vegetable and animal oils and fats. Stabilizing agents, wetting and emulsifying agents, salts for varying the osmotic pressure or buffers for securing an adequate pH value, and skin penetration enhancers can be used as auxiliary agents. Preservatives and other additives may also be present such as, for example, antimicrobials, antioxidants, chelating agents, and inert gases and the like. In one embodiment, a subject agent formulation comprises additional anti-mycobacterial and/or anti-bacterial agent(s).

A subject agent can be administered in the absence of agents or compounds that might facilitate uptake by target cells. A subject agent can be administered with compounds that facilitate uptake of a subject agent by target cells (e.g., by macrophages) or otherwise enhance transport of a subject agent to a treatment site for action. Absorption promoters, detergents and chemical irritants (e.g., keratinolytic agents) can enhance transmission of a subject agent into a target tissue (e.g., through the skin). For general principles regarding absorption promoters and detergents which have been used with success in mucosal delivery of organic and peptide-based drugs, see, e.g., Chien, *Novel Drug Delivery Systems*, Ch. 4 (Marcel Dekker, 1992). Examples of suitable nasal absorption promoters in particular are set forth at Chien, supra at Ch. 5, Tables 2 and 3; milder agents are preferred. Suitable agents for use in the method of this invention for mucosal/nasal delivery are also described in Chang, et al., *Nasal Drug Delivery*, "Treatise on Controlled Drug Delivery", Ch. 9 and Tables 3-4B thereof, (Marcel Dekker, 1992). Suitable agents which are known to enhance absorption of drugs through skin are described in Sloan, Use of Solubility Parameters from Regular Solution Theory to Describe Partitioning-Driven Processes, Ch. 5, "Prodrugs: Topical and Ocular Drug Delivery" (Marcel Dekker, 1992), and at places elsewhere in the text. All of these references are incorporated herein for the sole purpose of illustrating the level of knowledge and skill in the art concerning drug delivery techniques.

A colloidal dispersion system may be used for targeted delivery of the subject agent to specific tissue. Colloidal dispersion systems include macromolecule complexes, nanocapsules, microspheres, beads, and lipid-based systems including oil-in-water emulsions, micelles, mixed micelles, and liposomes.

Liposomes are artificial membrane vesicles which are useful as delivery vehicles in vitro and in vivo. It has been shown that large unilamellar vesicles (LUV), which range in size from 0.2-4.0 Fm can encapsulate a substantial percentage of an aqueous buffer comprising large macromolecules. RNA and DNA can be encapsulated within the aqueous interior and be delivered to cells in a biologically active form (Fraley, et al., (1981) *Trends Biochem. Sci.,* 6:77). The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidylglycerols, where the lipid moiety contains from 14-18 carbon atoms, particularly from 16-18 carbon atoms, and is saturated. Illustrative phospholipids include egg phosphatidylcholine, dipalmitoylphosphatidylcholine and distearoylphosphatidylcholine.

Where desired, targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticulo-endothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various well known linking groups can be used for joining the lipid chains to the targeting ligand (see, e.g., Yanagawa, et al., (1988) *Nuc. Acids Symp. Ser.,* 19:189; Grabarek, et al., (1990) *Anal. Biochem.,* 185:131; Staros, et al., (1986) *Anal. Biochem.* 156:220 and Boujrad, et al., (1993) *Proc. Natl. Acad. Sci. USA,* 90:5728). Targeted delivery of a subject agent can also be achieved by conjugation of a subject agent to a the surface of viral and non-viral recombinant expression vectors, to an antigen or other ligand, to a monoclonal antibody or to any molecule which has the desired binding specificity.

Utility

The subject isolated cells and the subject active agents are useful in research, screening, and therapeutic applications. Subject cells are useful as research tools for investigating the mechanism of immunodeficiency virus latency. The subject cells are also useful in screening methods for identifying agents that reactivate latent immunodeficiency virus, and agents that block reactivation of latent immunodeficiency virus, which methods are described above. The subject agents are useful in treatment methods, as described below.

Treatment Methods

The invention further provides methods of treating an immunodeficiency virus infection in an individual; methods of reducing the reservoir of latent immunodeficiency virus in an individual. The methods generally involve administering to an individual in need thereof an effective amount of a subject agent that activates latent immunodeficiency virus. In many embodiments, the agent is administered as part of a combination therapy with at least one other anti-viral therapeutic agent.

The invention further provides methods of blocking reactivation of latent immunodeficiency virus in an individual. The methods generally involve administering to an individual in need thereof an effective amount of a subject agent that blocks activation of latent immunodeficiency virus. In many embodiments, the agent is administered as part of a combination therapy with at least one other anti-viral therapeutic agent.

An effective amount of a subject agent that reactivates latent HIV is an amount that reactivates latent HIV and reduces the reservoir of latent HIV in an individual by at least about 20%, at least about 30%, at least about 40%, at least about 50%, at least about 60%, at least about 70%, at least about 80%, or at least about 90%. A "reduction in the reservoir of latent HIV" (also referred to as "reservoir of latently infected cells") is a reduction in the number of cells in the individual that harbor a latent HIV infection. Whether the reservoir of latently infected cells is reduced can be determined using any known method, including the method described in Blankson et al. (2000) *J. Infect. Disease* 182 (6):1636-1642.

In general, reactivation of latent HIV in a cell results in death of the cell. Thus, in some embodiments, an effective amount of a subject agent that reactivates latent HIV is an amount that amount of a subject agent that reactivates latent HIV is an amount that kills $10^2$, $5 \times 10^2$, $10^3$, $5 \times 10^3$, $10^4$, $5 \times 10^4$, $10^5$, or more, cells in an individual, which cells harbor latent HIV.

The amount of subject agent that is administered will vary with the nature of the drug. As one non-limiting example, a subject agent can be administered in the range of about 0.2 to 20 mg/kg/day. The determination of how large a dosage to be used may be determined using the small animal model and relating the dosage based on pharmacokinetics, e.g. with equations predictive of interspecies scaling. Usually, the lowest effective dose will be used.

An agent is administered once a day, twice daily, twice a week, or three times per week, for a period of from about 24 hours to about 7 days, from about 7 days to about 2 weeks, from about 2 weeks to about 4 weeks, from about 4 weeks to about 8 weeks, from about 8 weeks to about 12 weeks, from about 12 weeks to about 24 weeks, or longer.

Routes of Administration

A subject agent is administered to an individual using any available method and route suitable for drug delivery.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the subject agent and/or the desired effect on the immune response. The subject agent can be administered in a single dose or in multiple doses, and may encompass administration of booster doses, to maintain the desired effect.

A subject agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Inhalational routes of administration (e.g., intranasal, intrapulmonary, and the like) are particularly useful in stimulating an immune response for prevention or treatment of infections of the respiratory tract. Such means include inhalation of aerosol suspensions or insufflation of a composition of the invention. Nebulizer devices, metered dose inhalers, and the like suitable for delivery of compositions to the nasal mucosa, trachea and bronchioli are well known in the art and will therefore not be described in detail here. For general review in regard to intranasal drug delivery, see, e.g., Chien, *Novel Drug Delivery Systems*, Ch. 5 (Marcel Dekker, 1992).

Parenteral routes of administration other than inhalation administration include, but are not necessarily limited to, topical, transdermal, subcutaneous, intramuscular, intraorbital, intraspinal, intrasternal, and intravenous routes, i.e., any route of administration other than through the alimentary canal. Parenteral administration can be carried to effect systemic or local delivery of subject agent.

Systemic administration typically involves intravenous, intradermal, subcutaneous, or intramuscular administration or systemically absorbed topical or mucosal administration of pharmaceutical preparations. Mucosal administration includes administration to the respiratory tissue, e.g., by inhalation, nasal drops, ocular drop, etc.; anal or vaginal routes of administration, e.g., by suppositories; and the like. A subject agent can also be delivered to the subject by enteral administration. Enteral routes of administration include, but are not necessarily limited to, oral and rectal (e.g., using a suppository) delivery.

Any of a variety of methods can be used to determine whether a treatment method is effective. For example, methods of determining whether the methods of the invention are effective in treating an immunodeficiency virus infection, are any known test for indicia of immunodeficiency virus infection, including, but not limited to, measuring viral load, e.g., by measuring the amount of immunodeficiency virus in a biological sample, e.g., using a polymerase chain reaction (PCR) with primers specific for an immunodeficiency virus polynucleotide sequence; detecting and/or measuring a polypeptide encoded by an immunodeficiency virus, e.g., p24, gp120, reverse transcriptase, using, e.g., an immunological assay with an antibody specific for the polypeptide; and measuring CD4 cell count in the individual. Methods of assaying an immunodeficiency virus infection (or any indicia associated with an immunodeficiency virus infection) are known in the art, and have been described in numerous publications such as *HIV Protocols* (*Methods in Molecular Medicine*, 17) N. L. Michael and J. H. Kim, eds. (1999) Humana Press.

Combination Therapies

A subject agent can be administered to an individual in combination (e.g., in the same formulation or in separate formulations) with another therapeutic agent ("combination therapy"). The subject agent can be administered in admixture with another therapeutic agent or can be administered in a separate formulation. When administered in separate formulations, a subject agent and another therapeutic agent can be administered substantially simultaneously (e.g., within about 60 minutes, about 50 minutes, about 40 minutes, about 30 minutes, about 20 minutes, about 10 minutes, about 5 minutes, or about 1 minute of each other) or separated in time by about 1 hour, about 2 hours, about 4 hours, about 6 hours, about 10 hours, about 12 hours, about 24 hours, about 36 hours, or about 72 hours, or more.

Therapeutic agents that can be administered in combination with an effective amount of an agent that inhibits one or more immunodeficiency virus functions, which functions include, but are not limited to, viral replication; viral protease activity; viral reverse transcriptase activity; viral entry into a cell; viral integrase activity; activity of one or more of Rev, Tat, Nef, Vpr, Vpu, and Vif; and the like.

Therapeutic agents that can be administered in combination therapy, include, but are not limited to, anti-inflammatory, anti-viral, anti-fungal, anti-mycobacterial, antibiotic, amoebicidal, trichomonocidal, analgesic, anti-neoplastic, anti-hypertensives, anti-microbial and/or steroid drugs, to treat antiviral infections. In some embodiments, patients are treated with a subject agent in combination with one or more of the following; beta-lactam antibiotics, tetracyclines, chloramphenicol, neomycin, gramicidin, bacitracin, sulfonamides, nitrofurazone, nalidixic acid, cortisone, hydrocortisone, betamethasone, dexamethasone, fluocortolone, prednisolone, triamcinolone, indomethacin, sulindac, acyclovir, amantadine, rimantadine, recombinant soluble CD4 (rsCD4), anti-receptor antibodies (e.g., for rhinoviruses), nevirapine, cidofovir (Vistide™), trisodium phosphonoformate (Foscarnet™), famcyclovir, pencyclovir, valacyclovir, nucleic acid/replication inhibitors, interferon, zidovudine (AZT, Retrovir™), didanosine (dideoxyinosine, ddI, Videx™), stavudine (d4T, Zerit™), zalcitabine (dideoxycytosine, ddC, Hivid™), nevirapine (Viramune™), lamivudine (Epivir™, 3TC), protease inhibitors, saquinavir (Invirase™, Fortovase™), ritonavir (Norvir™), nelfinavir (Viracept™), efavirenz (Sustiva™), abacavir (Ziagen™), amprenavir (Agenerase™) indinavir (Crixivan™), ganciclovir, AzDU, delavirdine (Rescriptor™), kaletra, trizivir, rifampin, clathiromycin, erythropoietin, colony stimulating factors (G-CSF and GM-CSF), non-nucleoside reverse transcriptase inhibitors, nucleoside inhibitors, adriamycin, fluorouracil, methotrexate, asparaginase and combinations thereof.

Subjects Suitable for Treatment

The methods of the present invention are suitable for treating individuals who have an immunodeficiency virus infection; who are at risk of contracting an immunodeficiency virus infection; and who were treated for an immunodeficiency virus infection, but who relapsed. Such individuals include, but are not limited to, individuals with healthy, intact immune systems, but who are at risk for becoming HIV infected ("at-risk" individuals). At-risk individuals include, but are not limited to, individuals who have a greater likelihood than the general population of becoming HIV infected. Individuals at risk for becoming HIV infected include, but are not limited to, individuals at risk for HIV infection due to sexual activity with HIV-infected individuals; intravenous drug users; individuals who may have been exposed to HIV-infected blood, blood products, or other HIV-contaminated body fluids; babies who are being nursed by HIV-infected mothers.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric. Standard abbreviations may be used, e.g., h, hour(s); s or sec, second(s); min, minute(s); ml, milliliter; U, unit(s); and the like.

Example 1

Isolation, Purification, and Characterization of Cell Lines Carrying a Latent HIV Methods Viral Production and Cell Infections For the production of viral particles containing the HIV-derived vector LTR-Tat-IRES-GFP, $5 \times 10^6$ 293T cells were transfected with plasmids pEV731 (10 µg), pCMV-R8.91 (6.5 µg), and pMD.G (3.5 µg) in 10-cm dishes. (LTR, long terminal repeat; IRES, internal ribosome entry site; GFP, green fluorescent protein). After 16 hours, the medium was replaced, and supernatants containing viral particles were harvested 24 hours later. The number of infective particles per ml was established by infecting $2 \times 10^5$ Jurkat cells with different amounts of viral suspension. The titer of the virus stock was measured by flow cytometry analysis of GFP expression 96 hours after infection.

To obtain a random library of clones containing the vector LTR-Tat-IRES-GFP integrated, Jurkat cells were infected at an MOI (multiplicity of infection) of 0.1 followed by serial dilution and plating in 96-well plates. Individual clones obtained after 3 weeks were analyzed by flow cytometry for GFP expression. For the purification of latently infected cells, Jurkat cells were infected with the LTR-Tat-IRES-GFP viral stock at an MOI of 0.1 and kept in culture for at least 96 h. GFP-negative (GFP$^-$) and GFP-positive (GFP$^+$) cells were separated by fluorescence activated cell sorting (FACS) and further cultured. One week later, GFP$^-$ cells were incubated with 10 nM TPA or 10 ng/ml TNF-α for 17 h.

The resulting GFP$^+$ cells were sorted as a population and kept in culture or sorted into 96-well plates at 1 cell per well to generate clonal cell lines. Viral particles harboring an LTR-Tat vector were obtained as described above by transfecting 293T cells with plasmids pEV695, pCMV-R8.91 and pMD.G, which plasmids are described in Jordan et al. (2001) *EMBO J.* 20:1726-1738.

Cell Culture, Transfections and Cell Treatments

Jurkat cells were grown in RPMI 1640 medium (Mediatech Cellgro, Herndon, Va.) supplemented with 10% fetal bovine serum, 100 U/ml of penicillin, 100 µg/ml of streptomycin, and 2 mM L-glutamine at 37° C. under a 95% air/5% $CO_2$ atmosphere. Peripheral blood mononuclear cells (PBMCS) were cultivated in the same medium supplemented with 100 U/ml human interleukin (hIL)-2 and were phytohemagglutinin (PHA)-stimulated (5 µg/ml) once every two weeks. 293T cells were grown under the same conditions as Jurkat cells in Dulbecco's modification of Eagle's medium (Mediatech Cellgro, Herndon, Va.). 293T cells were routinely transfected with calcium phosphate. Jurkat cells ($10^7$ cells/0.4 ml serum-free medium) were electroporated in 0.4-cm gap cuvettes at 250 V and 950 mA (Gene Pulser II, Biorad, Hercules, Calif.). Plasmid DNA for transfections was purified with the Qiagen Plasmid Maxi kit, followed by phenol extraction and ethanol precipitation. To test the HIV promoter inducibility, Jurkat-derived clones were incubated for 17 h with 10 nM tetradecanoyl phorbol acetate (TPA), 10 ng/ml TNF-α, 5 µg/ml PHA, 1 µM ionomycin, 5 µg/ml anti-CD3 antibody, 400 nM Trichostatin A (TSA). Incubations with 5 µM aza-dC lasted for 48 h.

Flow Cytometry Analysis and Sorting

Cells were washed in PBS and resuspended in PBS containing 1% paraformaldehyde. GFP fluorescence was measured with a FACScalibur machine (Becton Dickinson, San Jose, Calif.). A two-parameter analysis to distinguish GFP-derived fluorescence from background fluorescence was used: GFP was measured in FL1 and cellular autofluorescence was monitored in FL2. Electronic compensation was applied during analysis. Analysis was gated on live cells according to forward and side scatter. A gate (R2) containing GFP-positive cells was drawn compared to an uninfected control, and the data shown refer to the percentage of cells in R2 or mean fluorescence intensity (MFI) of those cells. Results shown throughout the manuscript are representative three independent experiments, except when libraries of clones were analyzed. Cell sorting was carried out with a FACSVantage (Becton Dickinson, San Jose, Calif.).

Southern and Colony Hybridizations

Genomic DNA from infected Jurkat cells was extracted with the DNeasy Tissue kit (Qiagen, Valencia, Calif.). Southern hybridization was performed on digested DNA with [α-$^{32}$P]dCTP-labeled probes (Multiprime DNA labeling system, Amersham Pharmacia Biotech, Piscataway, N.J.) as described previously. Jordan et al. supra. For probes, DNA fragments internal to the pEV731 retroviral vector were generated by PCR amplification: a 1.4-kb fragment extending between the 5' LTR and Tat was generated with primers EV1048 (5'-GTGGCGCCCGAACAGGGACC-3'; SEQ ID NO:01) and EV1049 (antisense, 5'-CCGTC-GAGATCCGTTCACTA-3'; SEQ ID NO:02); a 171-bp fragment corresponding to the 5' end of the LTRs was produced with primers EV976 (5'-GCTAATTCACTCCCAACGAA-GAC-3'; SEQ ID NO:03) and EV1333 (antisense, 5'-GCT-TCTTCTACCTTCTCTTGCTC-3'; SEQ ID NO:04); a 70-bp fragments for the 3' end of the LTRs was generated with primers EV984 (5'-GCCCGTCTGTTGTAT-GACTCTG-3'; SEQ ID NO:05) and primer EV934 (antisense, 5'-CGCCACTGCTAGAGATTTTCCAC-3'; SEQ ID NO:06).

Alphoid PCR Amplifications and Quantitative PCR

To quantify the occurrence of integration close to alphoid repeats, we developed a PCR assay based on previously reported methods for Alu elements. We used a human alpha satellite monomer consensus sequence derived from 293 cloned monomers of diverse chromosomal origins to design oligonucleotides α1 (5'-AGACAGAAGCATTCTSAGAA-3'; SEQ ID NO:07), α2 (5'-ATCACAAAGNAGTTTCTSA-GAAT-3'; SEQ ID NO:08), α3 (5'-TTTSATWGAGCAGNT-TKGAAAC-3'; SEQ ID NO:09) and α4 (5'-AAAGAGTGTTTCMAANCTGCTCW-3'; SEQ ID NO:10). During the first PCR reaction, genomic DNA was amplified with primer A (EV1371, 5'-AGGCAAGCTTTAT-TGAGGCTTAAGC-3'; SEQ ID NO:11; antisense LTR) and either primer α1, α2, α3, α4, Alu (EV1255, 5'-TCCCAGC-TACTCGGGAGGCTGAGG-3'; SEQ ID NO:12) or B (EV1372, 5'-CACACACAAGGCTACTTCCCT-3'; SEQ ID NO:13; LTR) as a positive control for the presence of the LTR presence.

As negative controls, amplifications with no primer or with primer A alone were performed. Taq DNA polymerase (0.75 U/25 µl reaction; Life Technologies, Rockville, Md.), 200 nM each dNTP, and 500 nM each primer were used, and the reaction was run with the following program: (a) 3 min at 94° C.; (b) 30 cycles of 30 sec at 94° C., 30 sec at 53° C., and 4 min at 72° C.; and (c) 10 min at 72° C.

A second nested PCR amplification was carried out by using 1 µl of the first reaction with primers B (EV1372) and C (EV1373, 5'-GCCACTCCCCIGTCCCGCCC-3'; SEQ ID NO:14; antisense LTR), which allows amplification of a fragment of the LTR. This second PCR was done using same conditions as the first one, but the extension time was 1 min and amplification was run for 25 cycles. PCR products were analyzed by ethidium bromide/agarose gel electrophoresis and DNA bands were quantified with the EagleSight software (Stratagene, La Jolla, Calif.).

Real-time PCR (TaqMan) was also used to quantify integration of HIV-derived vectors close to alphoid or Alu repeats, using a modification of a published protocol. Butler et al. (2001) Nat. Med. 7:631-634. A first PCR was carried out for 25 cycles as described above but, instead of primer A, the LTR primer D (EV933, 5'-GAGCCCTCAGATGCT-GCATATAAG-3'; SEQ ID NO:15) was used in combination with primers α1-4 or Alu to amplify genomic regions downstream of the 3'LTR. For the nested real-time PCR, internal LTR primers E (EV1441, 5'-AACTAGGGAAC-CCACTGCTTAAG-3'; SEQ ID NO:16) and F (EV934, 5'-CGCCACTGCTAGAGATTTTCCAC-3'; SEQ ID NO:06; antisense) were used. An aliquot (1 µl) of the first amplification product was amplified with 200 nM of each of the specific primers and 100 nM of the LTR-specific TaqMan probe G (EV1444, 5'-6 FAM-ACACTACTTGAAGCACT-CAAGGCAAGCTTT-TAMRA-3'; SEQ ID NO:17) using the TaqMan Universal PCR Master mix (Perkin Elmer Applied Biosystems, Foster City, Calif.). The reaction was run for 40 cycles (15 sec at 95° C. plus 1 min at 60° C.), in an AbiPrism 7700 Sequence Detector (Perkin Elmer Applied Biosystems, Foster City, Calif.). Quantification was performed as recommended by Perkin Elmer.

Sequencing of Integrated Provirus

To check for the occurrence of mutations, the 5' LTR from selected clones was amplified (823-bp fragment) from genomic DNA with primers EV976 (5'-GCTAATTCACTC-CCAACGAAGAC-3'; SEQ ID NO:03; 5' end of LTR) and EV987 (antisense, 5'-TCGCTTTCAGGTCCCTGTTCG-3'; SEQ ID NO:18; gag region downstream 5'LTR). A Tat-IRES-GFP' fragment (1,307 bp) was amplified with primers EV1 140 (5'-CCATCGATGCCACCATGGAGCCAG-TAGA-3'; SEQ ID NO:19; 5' end of Tat) and EV1253 (antisense, 5'-AGGGTGTCGCCCTCGAA-3'; SEQ ID NO:20; internal to GFP). Pfu DNA polymerase (Stratagene, La Jolla, Calif.) was used and the reaction was run with the following program: (a) 45 sec at 94° C.; (b) 30 cycles of 45 sec at 94° C., 45 seconds at 58° C., and 1.5 minutes at 72° C.; and (c) 10 minutes at 72° C.

The amplified product was purified from ethidium bromide-containing 1%-agarose gel with the GenClean Spin kit (Qbiogene, Carlsbad, Calif.) and cloned in the pCR-Blunt vector provided in the Zero Blunt PCR Cloning kit (Invitrogen, Carlsbad, Calif.). Two to four recombinant clones containing the expected DNA insert were sequenced with primers M13 Forward and M13 Reverse and the Big Dye d-Rhodamine Terminator Ready Reaction kit (Perkin Elmer Applied Biosystems, Foster City, Calif.).

HIV-Specific mRNA Measurements

RNA was isolated using TRIzol (Invitrogen) followed by digestion with RQ1 DNase (Promega). First strand cDNA was synthesized using Superscript II (Invitrogen). Taqman PCR was performed on an ABIprism 7700 detector using the following primer/probe set: primer 1: 5'-GTGTGC-CCGTCTGTTGTGTGA-3' (SEQ ID NO:21); primer 2: 5'-GCCACTGCTAGAGATTTTCCA-3' (SEQ ID NO:22); probe 5'-CTGGTAACTAGAGATCCC-3' (SEQ ID NO:23). The GAPDH primer/probe set was purchased from Applied Biosystems.

Construction of HIV-R7/E⁻/GFP Molecular Clone

The HIV molecular clone (HIV-R7/E⁻/GFP) was constructed by introducing a frameshift mutation in the env gene (by filling-in NdeI site with T4 polymerase) in the backbone of HIV-R7/3/GFP. Bieniasz and Cullen (2000) J. Virol. 74:9868-9877.

Sequencing of Flanking Genomic Regions

A variety of strategies were used to clone genomic DNA at the integration site of latent clones. Inverse PCR was used to obtain the genomic region flanking the 3' LTR on the integrated provirus of clone #82. Briefly, genomic DNA was digested with NcoI (cleavage site between IRES-GFP), and the resulting products were circularized by incubating with T4 DNA ligase (New England Biolabs, Beverly, Mass.). A nested series of three inverse PCRs were performed with 3 primers for GFP (EV1253, EV1335 (5'-GGTCTTGTAGT-TGCCGTCGTC-3'; SEQ ID NO:24) and EV1336 (5'-GAA-GAAGATGGTGCGCTCC-3'; SEQ ID NO:25); antisense) and 3 primers for LTR (EV933, EV996 (5'-TTGCCTG-TACTGGGTCTCTCTG-3'; SEQ ID NO:26) and EV984). Before cloning the amplification products, the presence of LTR-containing products was confirmed by Southern hybridization with the probe EV984/EV934 described above.

Once a particular clone was identified as containing the retroviral vector integrated close to alphoid or Alu repeats, a series of 2-3 nested PCR amplifications were carried out with alphoid (α1-4) or Alu (EV1255) primers and with primers for the HIV LTR (EV977 (5'-ATTCCATGCAG-GCTCACAGG-3'; SEQ ID NO:27), EV1332 (5'-GTGTAA-CAAGCGGGTGTTCTCTC-3'; SEQ ID NO:28) and EV1333 for the 5'LTR, or EV933, EV996 and EV984 for the 3' LTR.

To clone the integration site from clones that were not flanked by alphoid repeats, we used ligation-mediated PCR (LM-PCR) (Schmidt et al. (2001) *Hum. Gene Ther.* 12:743-749). Briefly, genomic DNA was digested with NlaIII (New England Biolabs, Beverly, Mass.) and ligated to 100 pmoles of annealed linker cassette (oligonucleotides EV1534 5'-GACCCGGGAGATCTGAATTCAGTGGCA-CAGCAGTTAGG-3'; SEQ ID NO:29, and EV1535 5'-CCTAACTGCTGTGCCACTGAATTCAG-3'; SEQ ID NO:30). The ligation products were used as a template in a PCR amplification with retroviral primer EV996 and linker-specific primer EV1532 (5'-GACCCGGGAGATCT-GAATTC-3'; SEQ ID NO:31), that amplifies the 3' LTR and flanking genomic region. Next, an aliquot of the first PCR was used on a nested PCR with the retroviral primer EV984 (LTR) and linker-specific primer EV1533 (5'-AGTGGCA-CAGCAGTTAGG-3'; SEQ ID NO:32) to increase specificity of amplification.

In all cases, amplification products were cloned into pCR-Blunt vector and colony hybridization was used to screen for colonies harboring an LTR-containing fragment with probe EV976/EV1333 or EV984/EV934 described above. Selected clones were sequenced as described. BLAST (National Center for Biotechnology Information) was used to compare sequences with the human genome draft sequence and nucleotide database.

Sequence of Flanking Genomic Regions in PBMCs from HIV-Infected Patients

HIV integration site sequence in alphoid repeats. DNA was extracted from PBMCs from HIV-infected patients completely suppressed by highly active antiretroviral therapy.

Results

Establishment of an In Vitro Model of HIV-1 Latency

To determine whether unique integration events can lead to latency, we used an HIV-based retroviral vector containing the Tat and GFP open reading frames both under the control of the HIV promoter in the 5' long terminal repeat (LTR). We infected a culture of the lymphocytic cell line Jurkat with viral particles containing this vector and used differential fluorescence-activated cell sorting (FACS) based on GFP expression (FIG. 1A). First, we infected Jurkat cells with the LTR-Tat-IRES-GFP virus at a low MOI and isolated GFP-negative cells by FACS 4 days after infection (FIG. 1A). This population presumably harbored both uninfected cells and cells with transcriptionally silenced proviruses. To activate HIV expression, we treated this population with TPA or tumor necrosis factor alpha (TNF-α) and purified GFP-positive cells by FACS (FIG. 1A). These cells, representing less than 0.06% of the original population, corresponded to the latent phenotype: GFP-negative under basal conditions and GFP-positive after activation with TPA or TNF-α. By comparing the proportions of productively infected cells (4%) and cells exhibiting a latent phenotype (0.06%), we calculate that ~1.5% of infections (1 in 66) resulted in a latent state in this system. These cells were both grown as a group and individually sorted for further characterization. Reanalysis 17 days after sorting showed that a significant proportion of the cells had no GFP expression, indicating transcriptional silencing in the absence of TPA (FIG. 1A).

Individual cells exhibiting a latent phenotype were cloned and clonal cell lines were further characterized. Flow cytometry analysis of individual clones 4 weeks after their isolation showed low basal GFP expression (FIG. 1B-*left* panel). After TPA treatment, all clones were activated, and GFP levels reached a maximum that was relatively independent of basal GFP activity (FIG. 1B-*right* panel). Similar results were obtained after stimulation with TNF-α.

Examination of mRNA levels in these cell lines under repressed (-TNF-α) and activated conditions (+TNF-α) confirmed the presence of very low transcriptional levels under basal conditions and the activation of HIV transcription by TNF-α (FIG. 1C-*see* clone H2). Importantly, HIV-specific transcript levels after TNF-α treatment were of the same order of magnitude as mRNA levels measured in Jurkat cells acutely infected with wild type HIV (NL4-3) (FIG. 1C).

FIGS. 1A-C. Enrichment and purification of HIV-latently infected cells by FACS. (A) A schematic representation of our enrichment protocol is shown. See text for details. The percentage of GFP-positive cells obtained after infection (4%) or after TNF-α treatment of GFP-cells (0.06%) is shown. Similar data were obtained with TPA. (B) Clonal cell lines isolated using the procedure described above were analyzed for GFP expression under basal and stimulated conditions (24 hr treatment with TNF-α). (C) mRNA levels were measured for HIV and for GAPDH using TaqMan PCR in untreated and TNF-α-treated cell lines. Results are expressed as a percentage of mRNA levels measured in Jurkat cells acutely infected with $HIV_{NL4-3}$ (day 6 post-infection). Clone A72 is infected with an LTR-GFP construct (Jordan et al. (2001, supra), clone H2 is infected with the LTR-Tat-IRES-GFP vector while clones F11 and G10 are infected with HIV-R7/E−/GFP.

Figure 2C:
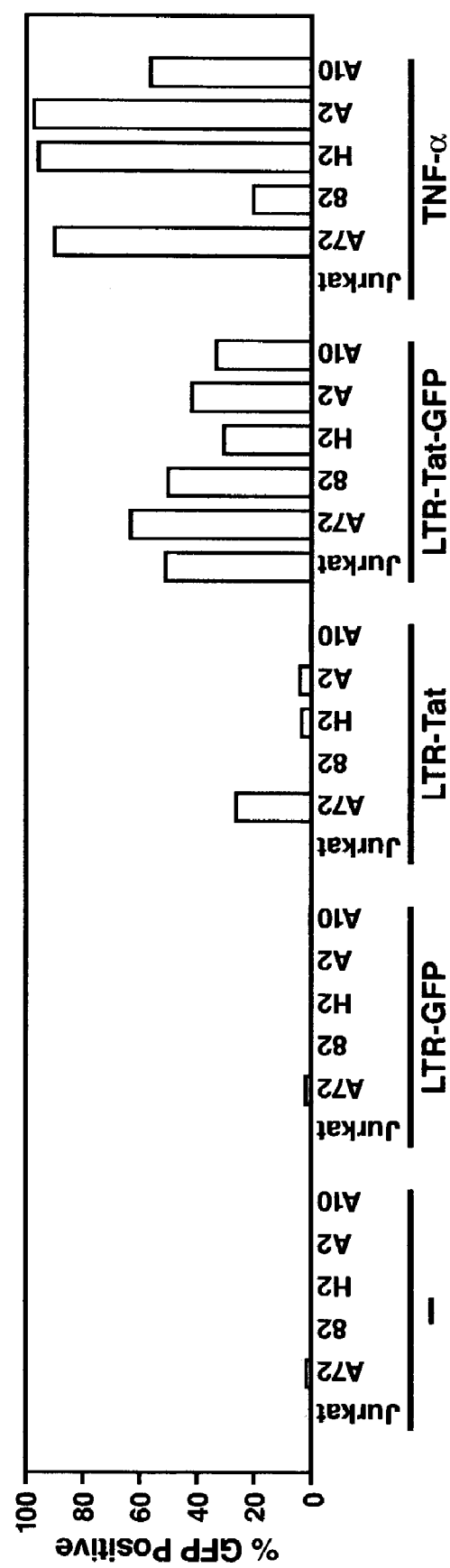

Mutations in a cellular factor important for HIV transcription, such as CDK9 or cyclin T1 for example, could be responsible for a latent phenotype. To test this possibility, we infected one of our latent cell line (clone 82) and control Jurkat cells with an LTR-GFP virus or with the LTR-Tat-IRES-GFP virus (FIG. 2A). Both cell lines produced similar amounts of GFP after infection with the LTR-GFP-virus (FIG. 2A). GFP levels were higher but also comparable in both cell lines after infection with the LTR-Tat-GFP virus (FIG. 2A). Similar results were observed in three other latent cells lines (clones H2, A2 and A10—FIG. 2C).

This experiment demonstrates that the cellular environment in latent cell lines can support HIV transcription and Tat transactivation with the same efficiency as control Jurkat cells and is therefore not responsible for the latent phenotype.

HIV transcription is characterized by an early, Tat-independent phase and a late, Tat-dependent phase. Since no GFP was produced by our latent cell lines, it is likely that Tat was not expressed since both proteins are located on a polycistronic mRNA. To test whether Tat alone was sufficient to reactivate latent HIV gene expression, we infected clone 82 with a HIV-derived retroviral vector expressing the Tat protein (LTR-Tat virus) (FIG. 2B). Infection of a Jurkat clone containing a single copy of an integrated LTR-GFP retroviral vector (clone A, described in Jordan et al. (2001) *EMBO J.* 20:1726-1738) with the same LTR-Tat virus stock showed high levels of GFP expression but had no effect in the latently infected cell line (FIG. 2B). Similar results were obtained after transfection of a Tat-expression plasmid into these cell lines. Similar results were also observed in three other latent cells lines (clones H2, A2 and A10) although weak stimulation of GFP expression was noted in clones H2 and A2 (FIG. 1C). We conclude that the latent HIV promoter is relatively unresponsive to Tat stimulation, suggesting that the blockage of transcription in this clone lies primarily at the level of transcription initiation.

FIGS. 2A-C. Characterization of latently infected clone. (A) Clone #82 is competent for basal and Tat-dependent HIV promoter activity. Clone #82 was infected with viral particles containing HIV-derived vectors LTR-GFP or LTR-Tat-IRES-GFP, and GFP expression was measured by flow cytometry. As a control, Jurkat cells were infected in parallel. (B) The integrated latent HIV promoter in clone #82 is unresponsive to Tat stimulation. Clone #82 was infected with a Tat-expression retroviral vector, or treated with TPA, as a positive control. As a control of the infection process and Tat expression, a clone containing a single integration of the HIV-derived LTR-GFP vector was infected in parallel. (C) HIV promoter activity (% of GFP positive cells in R2 gate) was measured in four latent clonal cell lines (82, H2, A2 and A10) 24 hr after infection with retroviral particles containing the following vectors: LTR-GFP, LTR-Tat, LTR-Tat-GFP or after treatment with TNFα. Control Jurkat cells and a cell line containing a stably integrated LTR-GFP retroviral construct (Jordan et al. (2001) supra) were used as controls.

Preferential HIV Integration in or Near Alphoid DNA in Latently Infected Cells

The basal activity of the HIV promoter is determined by a combination of cis- and trans-acting variables. The observations described above indicate that the cellular environment in each latent cell line is fully capable of supporting the transcription of the HIV genome and therefore points to the role of the site of integration of the provirus as a likely cause for low basal transcription. Accordingly, we isolated and sequenced the provirus integration sites in 8 distinct clonal cell lines (FIG. 3A) Mapping of the integration site on the human genome using BLAST showed that the retroviral vector had integrated in an alphoid repeat element in 4 out of 8 clones on chromosomes 7, 10 and 16 (FIG. 3A). The site of integration of 3 clones was identified in the human genome in non-alphoid repeat DNA while the site of integration in one clone did not yield significant homology to any region of the human genome (FIG. 3A).

Figure 3B:
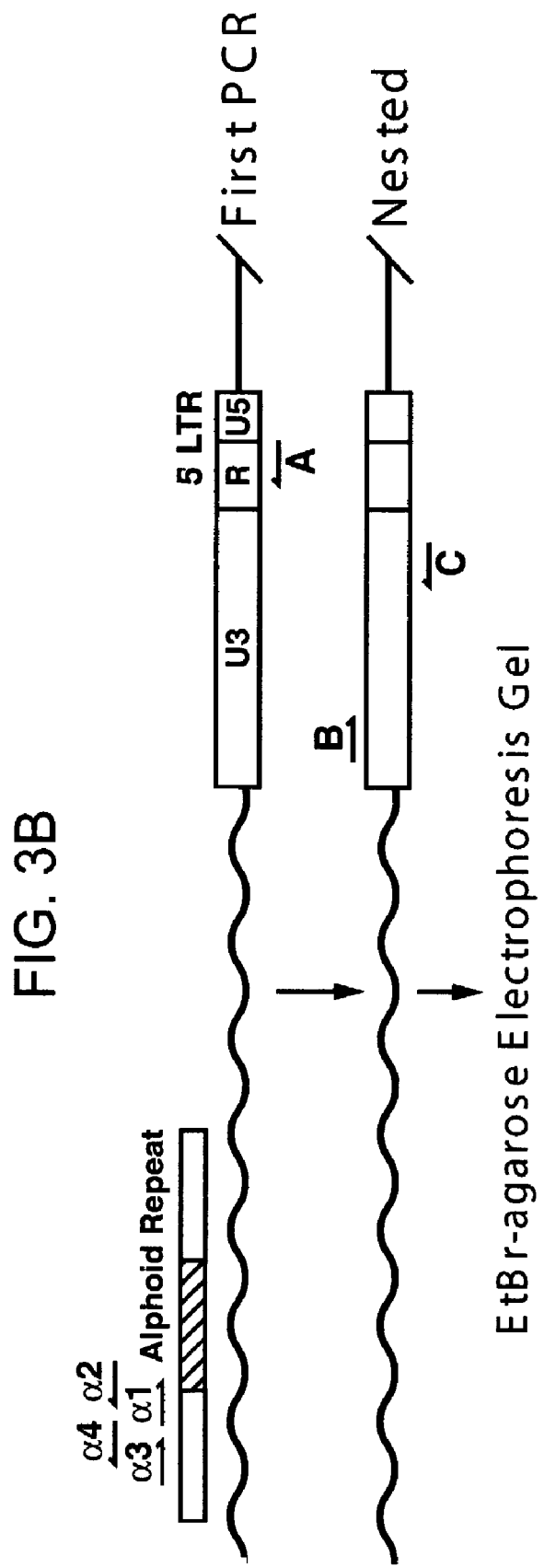

To confirm this observation, we developed a novel PCR assay in which degenerate primers matching alphoid DNA consensus sequence (α1, α2, α3, α4) are used in combination with an LTR specific primer (primer A)(FIG. 3A). Amplified products were detected with two nested primers in the LTR (primers B and C) (FIG. 3B). Since primers α1 and α3 are orientated in the same way in the alphoid repeat, a positive signal with one primer should be accompanied by a positive signal for the other (FIG. 3B). The same holds true for primers α2 and α4 (FIG. 3B). Similarly, a positive response with primers α1 and α3 would be accompanied by a negative signal for primers α2 and α4. Examination of the PCR reactions showed a perfect concordance with the sequencing data: clones 82, A7, H2 and F2 showed a positive PCR reaction and had a documented alphoid repeat integration while clones A1, A5, A10 and A11 tested negative in the PCR assay and did not integrate in an alphoid element.

For comparison, we subjected DNA obtained from a library of 34 random integrations (not sorted for a latent phenotype) to the same procedure (Jordan et al. (2001), supra). None of these 34 clones showed a pattern consistent with alphoid repeat integration, in agreement with previous reports that HIV integration in or near alphoid repeat elements is disfavored (Carteau et al. (1998) *J. Virol.* 72:4005-4014).

To examine the relative distribution of alphoid integration in latently vs. productively infected cells at a population level, we adapted the alphoid PCR assay to TaqMan PCR. Because Alu elements are randomly distributed within the genome, this analysis included a control using primers specific for the Alu element and the HIV LTR. The product amplified by this primer pair is assumed to represent random integration events within the genome and has been used as a reliable marker of HIV integration (Butler et al. (2001) *Nat. Med.* 7:631-634; Chun et al. (1997) *Proc. Natl. Acad. Sci. USA* 94:13193-13197; and Minami et al. (1995) *Genomics* 29:403-408. Results are therefore presented as the ratio of the alphoid-LTR product to the Alu-LTR product as an indication of the frequency of integration in or near alphoid DNA (FIG. 3D).

Figure 3C:
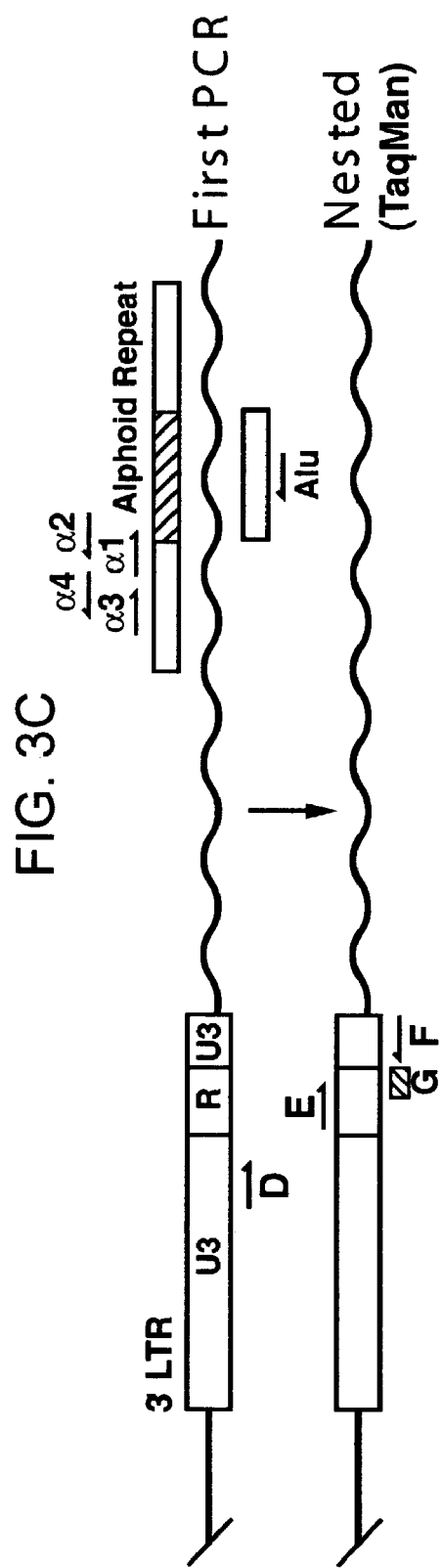
Figure 3D:
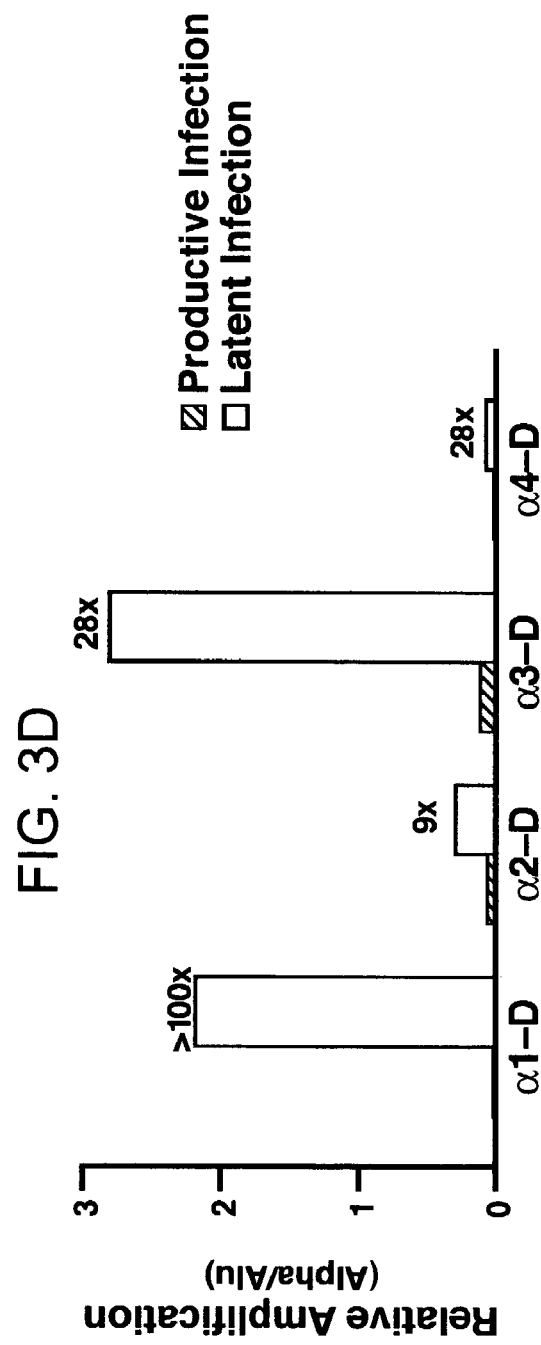

When cell populations corresponding to productively infected cells (GFP positive in first panel of FIG. 1A) were compared to latently-infected cell population (GFP positive in third panel of FIG. 1A), we observed preferential integration (9-fold to >100-fold enrichment) in or near alphoid repeats in latent cells in comparison to productively infected cells (FIG. 3D). Similar results were obtained after infection of human peripheral blood mononuclear cells (PBMCs) with the HIV-derived vector. Cloning and sequencing of several PCR products obtained after amplification with the alphoid specific primers confirmed that these contained HIV integration events into alphoid DNA.

FIG. 3 Latency is associated with preferred integration in or near alphoid repeats. (A) The sequence of integration site of the HIV vector is shown for 7 clonal cell lines aligned with the corresponding genomic sequence. The match in Genbank for each clone corresponded to Genbank accession number M93288 for clone 82, AL591625 for clone A1, AC023948 for clone A5, M16037 for clone A7, A1354920 for clone A10, AC019063 for clone H2 and AC079801 for clone F2. The sequence corresponding to the HIV promoter is indicated by a closed box. The chromosomal location of each integration site is shown and integration sites into alphoid repeat elements are indicated. (B) A nested PCR assay designed to quantify integration in or near alphoid repeats is schematically represented. The position of primers in the two sequential PCR reactions are show aligned with the HIV 5' LTR and a putative alphoid element in the genome. (C) Real-time PCR analysis of integration in or near alphoid repeats. Primer G represents an internal fluorescent primer used for the quantification of the TaqMan reaction. (D) Quantification of PCR products after TaqMan PCR analysis as indicated under D. Productively infected cells (GFP-positive cells in panel 1, FIG. 1A) (productive infection) are compared with latently infected cells (panel 4, FIG. 1A)(latent infection) using the Alu and alphoid PCR assay. Data is expressed as the relative signal intensity (alphoid/Alu). Numbers on top of bar indicates the ratio between latent and productive infection.

Transcriptional Activation of the HIV Promoter in Latently Infected Cells

Figure 4:
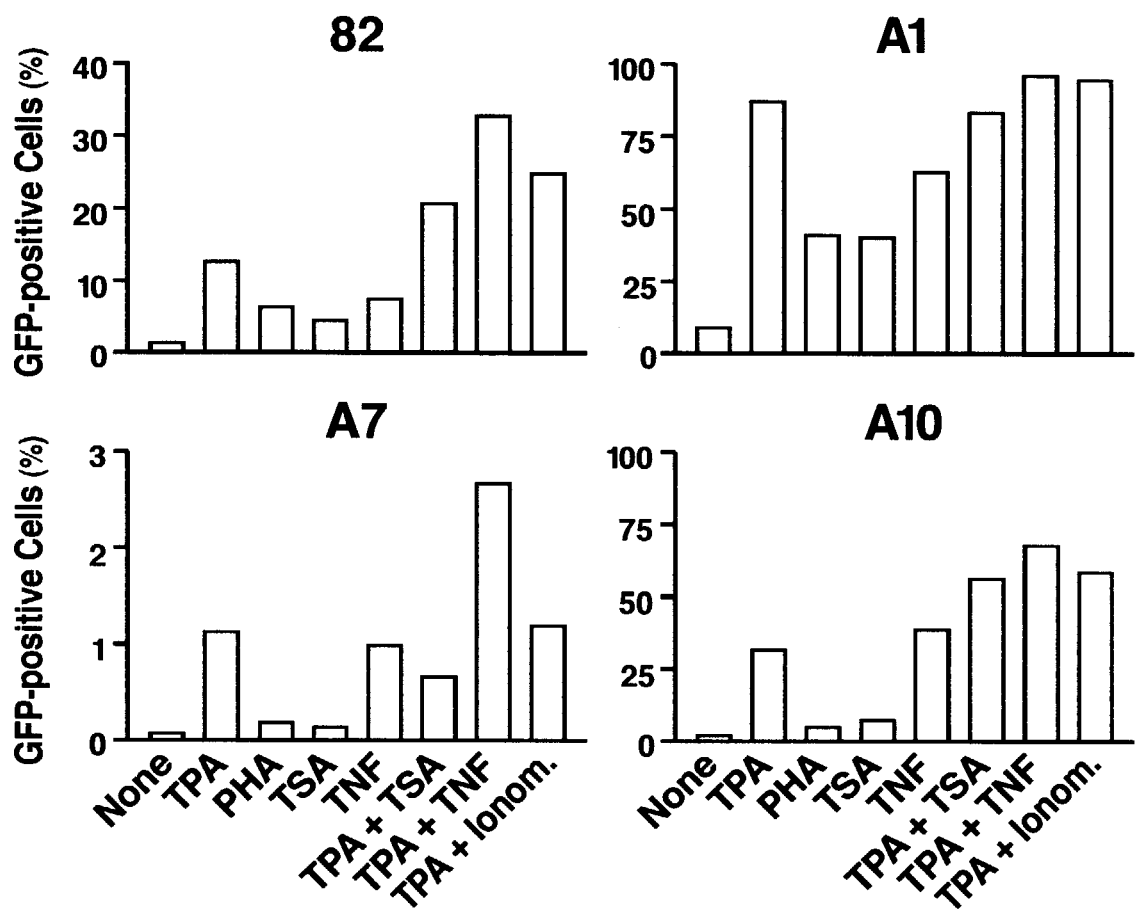
FIG. 4 depicts transcriptional activation of the HIV promoter in latently infected cells.

We have tested a number of biological and chemical agents for their ability to reactivate latent HIV expression. Several NF-κB activators, including TPA, TNF-α, and PHA, independently induced HIV expression, as expected since NF-κB strongly induces the HIV promoter activity. TPA was the strongest inducer tested (FIG. 4). All treatments increased the number of GFP-positive cells and the mean fluorescence intensity reflective of GFP levels. Incubation with anti-CD3 antibodies, which crosslink the surface T-cell receptors, an alternate pathway leading to NF-κB activation, also induced GFP expression. These results suggest that activation of the NF-κB pathway may boost HIV transcription initiation, the production of Tat, and transition to Tat-dependent transcriptional activation. Trichostatin A (TSA), an inhibitor of histone deacetylases also activated expression but to a lesser extent than NF-κB activators and in only some cell lines (see clones A1 as an example, FIG. 4A). Treatment with 5-axa-2-deoxycytidine (aza-dC), an inhibitor of DNA methylation, had little effect on the fraction of cells induced to transcribe HIV alone or in combination with a histone deacetylase inhibitor.

FIG. 4 Transcriptional activation of the HIV promoter in latently infected cells. Cells from clones 82, A1, A7 and A10 were treated as described in Methods with several indicated agents and LTR expression was measured by flow cytometry. Data are expressed as percentage of cells becoming GFP-positive after a 24 hr treatment.

Latent Cell Lines Containing a Full-Length Integrated HIV Genome

Figure 5A:
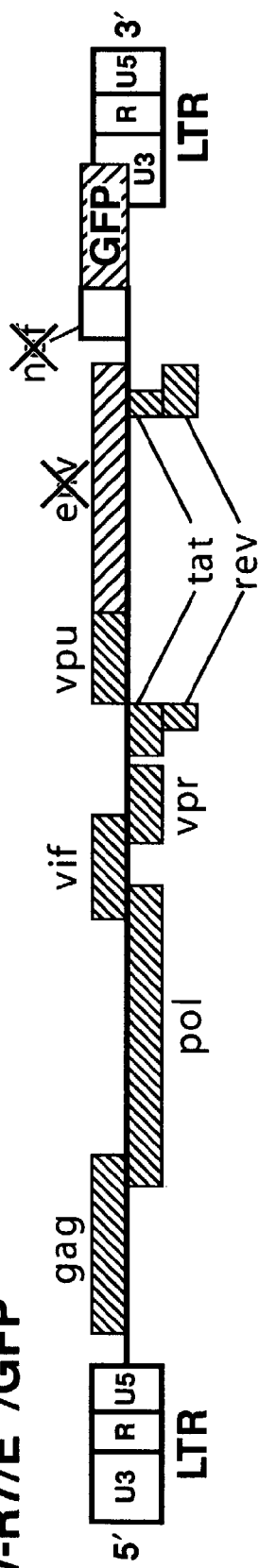
FIGS. 5A-C depict establishment of latently infected cell lines with a full-length HIV provirus.
Figure 5B:
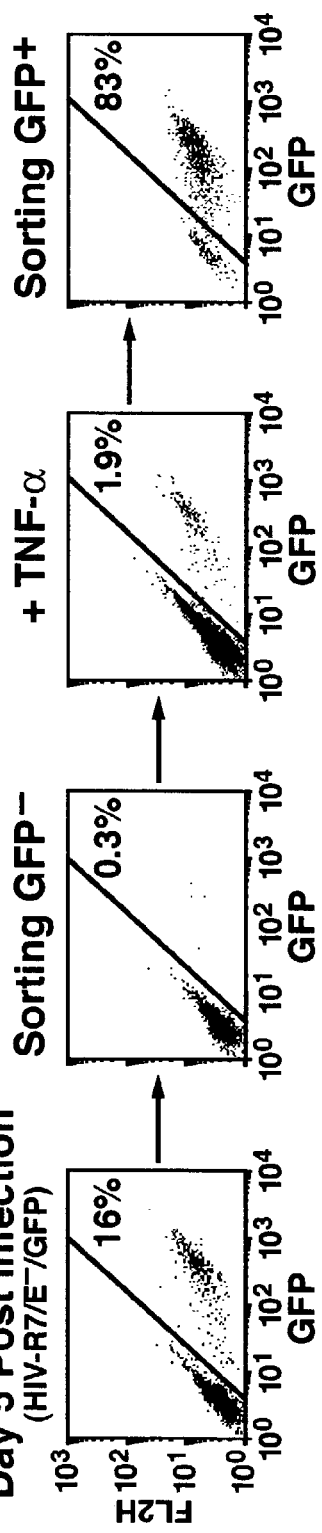

To confirm that HIV latency can be established in the context of a full length provirus, we used a recombinant HIV molecular clone containing the GFP open reading frame in place of the Nef gene (Bieniasz and Cullen (2000) *J. Virol.* 74:9868-9877) (HIV-R7/E−/GFP)(FIG. 5A). To restrict our analysis to a single infection cycle, the env gene was suppressed by introduction of a frameshift mutation. This defect was complemented by coexpression of a VSV-G envelope protein to generate pseudotyped viral particles. We infected a culture of the lymphocytic cell line Jurkat with viral particles containing this HIV genome and used differential fluorescence-activated cell sorting based on GFP expression to isolate GFP-negative cells by FACS 4 days after infection (FIG. 5B). Based on our previous experiments, we predicted that this population harbored both uninfected cells and cells with transcriptionally silenced proviruses. To activate HIV expression, we treated this population with TNF-α and observed that a small fraction of the cell population (1.9%) became positive. These activated cells were purified by FACS based on GFP expression levels (FIG. 5B). These cells were both grown as a group and individually sorted for further characterization.

Figure 5C:
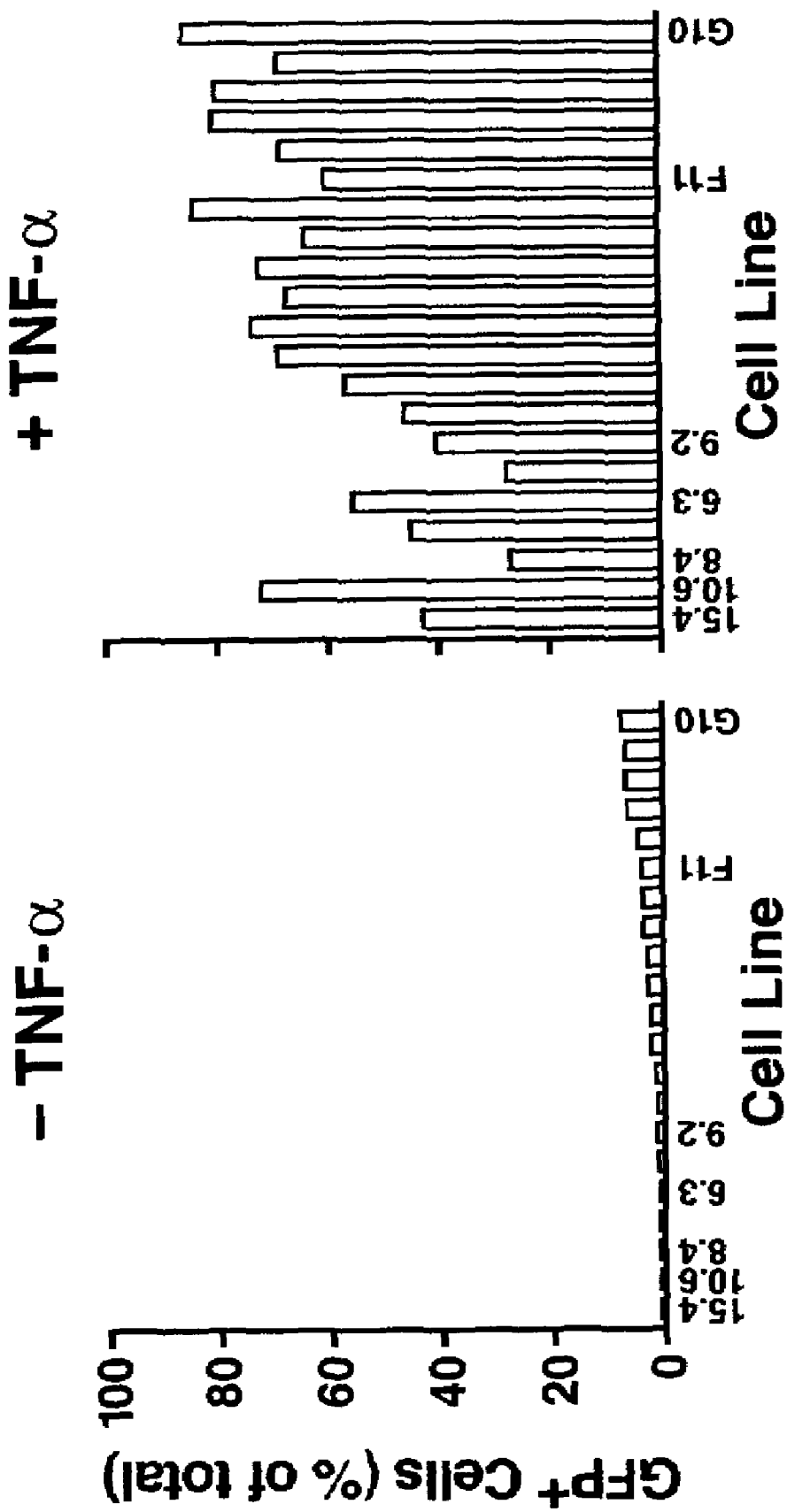

Reanalysis after sorting showed that a small proportion of the cells had no GFP expression, indicating transcriptional silencing has occurred after withdrawal of TNF-α (FIG. 5B). Flow cytometry analysis of individual clones showed low basal GFP expression (FIG. 5C). After TNF-α treatment, HIV expression was increased in all clones both in terms of the fraction of cells that became GFP positive (FIG. 5C) but also in terms of mean fluorescence intensity. Measurement of virus-specific mRNA showed that the mechanism of latency in these clones was controlled at the transcriptional level (FIG. 1C, clones F11 and G10). Levels of viral mRNA after activation were similar to those measured after a productive HIV infection (compare clones F11 and G10 with NL4-3, FIG. 1C). Analysis of HIV-specific protein expression in several clones by western blotting using an antiserum from an HIV-infected individual showed no detectable expression of HIV proteins under basal conditions. Treatment of the same clones with TNF-α led to a dramatic increase in HIV protein expression, particularly the gag p55 precursor (FIG. 5D).

FIG. 5. Establishment of latently infected cell lines with a full-length HIV provirus. (A) genome organization of a molecular clone of HIV encoding GFP and containing a frameshift mutation in env. (B) Schematic representation of protocol for enrichment of latently-infected cells after infection of Jurkat cells with HIV-R7/E−/GFP (see text for detail). (C) Clonal cell lines isolated using the procedure described above were analyzed for GFP expression under basal and stimulated conditions (24 hr treatment with TNF-α).

When the culture supernatants of the same clones were examined for HIV-specific p24 expression, no or low picogram amounts could be detected under basal conditions (Table I). Treatment with TNF-α led to a greater than a thousand-fold increase in p24 measurement for several representative clones (Table I). These observations demonstrate that transcriptional latency can also be established in the context of a full-length HIV infection.

TABLE I

| | GFP-Positive (%) | | GFP Signal (MFI) | | p24 (pg/ml) | |
|---|---|---|---|---|---|---|
| TNF-α | − | + | − | + | − | + |
| Clone 15.4 | <1 | 46 ± 6 | 6 ± 0.5 | 188 ± 34 | 7 ± 12 | 6,066 ± 1,960 |
| Clone 6.3 | <1 | 27 ± 9 | 5 ± 0.2 | 135 ± 43 | 0 | 10,100 ± 4,573 |
| Clone 8.4 | <1 | 77 ± 6 | 5 ± 0.3 | 488 ± 74 | 0 | 32,967 ± 10,537 |
| Clone 9.2 | <1 | 75 ± 7 | 7 ± 0.5 | 522 ± 61 | 23 ± 6 | 41,067 ± 9,100 |
| Clone 10.6 | <1 | 96 ± 1 | 5 ± 1.4 | 645 ± 45 | 14 ± 3 | 85,500 ± 5,981 |

We were able to amplify the integration site of provirus integrated into alphoid repeats from PBMCs from HIV-1-infected individuals treated with highly active antiretroviral therapy (data in FIG. 6).

Example 2

Identification of Agents that Reactivate Latent HIV

Figure 7:
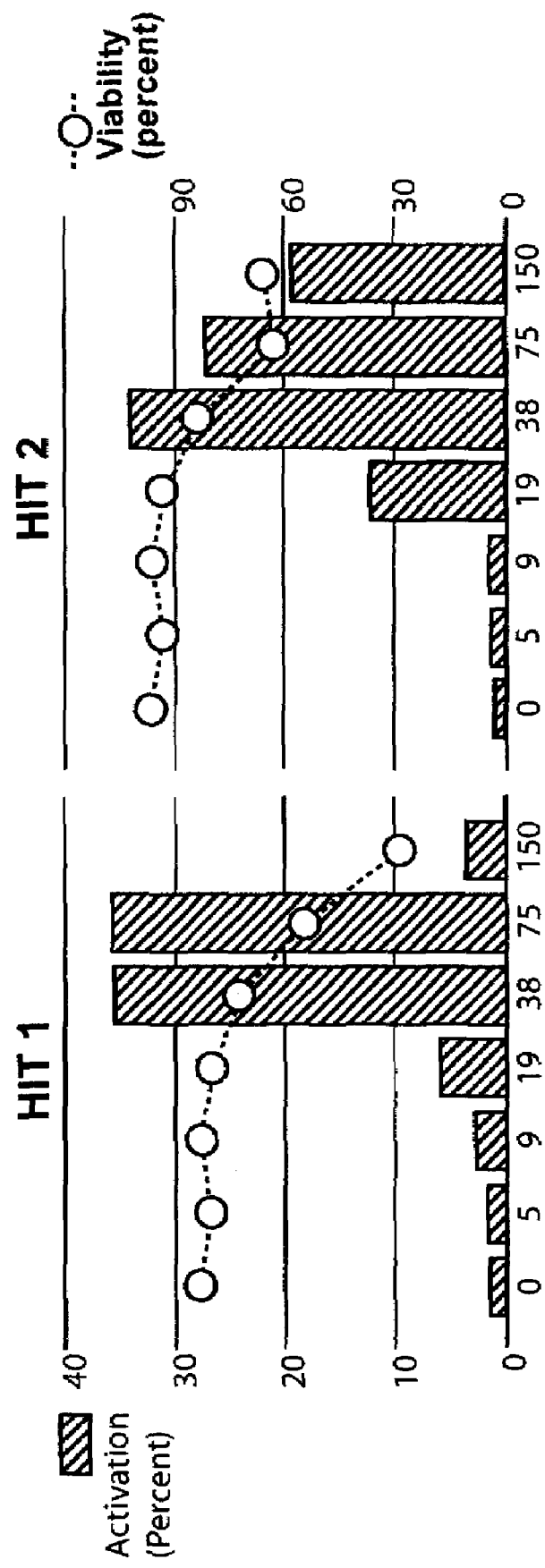
FIG. 7 depicts reactivation of latent HIV by two different agents.

We screened a library of 6,000 small molecules (library purchased from Chembridge, San Diego) using one of the cell lines containing a latent HIV-based retroviral vector. Viral expression was monitored by GFP expression, as described above. Two compounds were identified that reproducibly lead to an induction of HIV expression as measured by increased GFP expression. The results of a typical induction experiment in which we measured GFP expression in response to different concentrations of the two small molecules (Hit 1 and Hit2) are shown in FIG. 7. The structures of three representative active agents are shown below.

Hit #1-ID 766456-MW 366.3797-$C_{19}H_{18}N_4O_4$

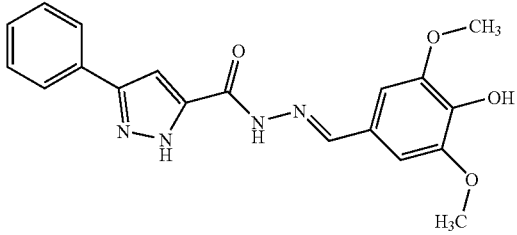

Hit #2-ID 681306-MW 294.3592-$C_{17}H_{18}N_4O$

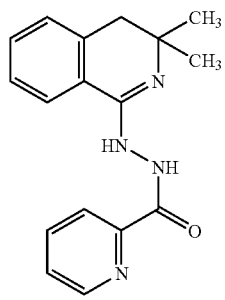

Hit #3-ID 671859-MW 317.3447-$C_{17}H_{19}NO_5$

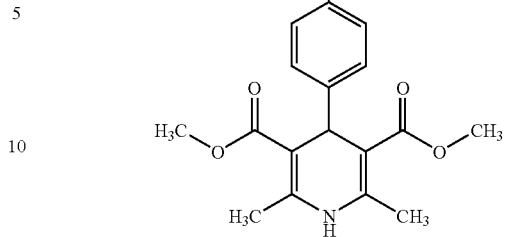

From the data presented above, it is evident that the instant invention provides isolated cells that harbor a latent immunodeficiency virus that is transcription competent, that can be reactivated, and that is an in vitro model for latent HIV infection in vivo. The cells are useful for investigating the nature of latency, and also in drug screening assays to identify agents that activate latent HIV. Identification of agents that activate latent HIV is important, as such agents are useful, particularly in conjunction with standard anti-HIV therapies, to reduce the reservoir of latent HIV.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. An isolated T cell line that comprises a recombinant transcription-competent immunodeficiency virus or vector integrated into the genome of the cell, wherein the virus or vector comprises a functional transactivation response element (TAR) and comprises a nucleotide sequence encoding a functional transactivator protein (Tat), wherein the immunodeficiency virus is latent under basal in vitro culture conditions, and wherein expression of the latent immunodeficiency virus can be reactivated.

2. The cell line of claim 1, wherein said cell is an immortalized cell line.

3. The cell line of claim 1, wherein said immunodeficiency virus is human immunodeficiency virus (HIV).

4. The cell line of claim 3, wherein said immunodeficiency virus is HIV-1.

5. An isolated immortalized cell that comprises a recombinant transcription-competent immunodeficiency virus or vector, wherein the virus or vector comprises a nucleotide sequence encoding a selectable marker operably linked to an immunodeficiency virus promoter, wherein said virus or vector is integrated into the genome of the cell, wherein the virus or vector comprises a functional transactivation response element (TAR) and comprises a nucleotide sequence encoding a functional transactivator protein (Tat), wherein the virus or vector is latent and transcriptionally silent under basal in vitro culture conditions, and wherein expression of the latent virus or vector can be reactivated.

6. The cell line of claim 1, wherein the latent virus or vector is reactivated by an activator of NF-κB or a histone deacetylase inhibitor.

7. The cell of claim 5, wherein the marker is a fluorescent protein.

8. The cell line of claim 6, wherein the activator of NK-κB is selected from tetradecanoyl phorbol acetate, tumor necrosis factor-α, phytohemagglutinin, and an anti-CD3 antibody.

9. The cell line of claim 6, wherein said histone deacetylase inhibitor is trichostatin A.

10. The cell of claim 5, wherein the latent virus or vector is reactivated by an activator of NF-κB or a histone deacetylase inhibitor.

11. The cell of claim 10, wherein the activator of NK-κB is selected from tetradecanoyl phorbol acetate, tumor necrosis factor-α, phytohemagglutinin, and an anti-CD3 antibody.

12. The cell of claim 10, wherein said histone deacetylase inhibitor is trichostatin A.

13. The cell of claim 5, wherein said immunodeflciency virus is a human immunodeficiency virus (HIV).

* * * * *

UNITED STATES PATENT AND TRADEMARK OFFICE
CERTIFICATE OF CORRECTION

PATENT NO. : 7,232,685 B2  Page 1 of 1
APPLICATION NO. : 10/323463
DATED : June 19, 2007
INVENTOR(S) : Eric M. Verdin et al.

It is certified that error appears in the above-identified patent and that said Letters Patent is hereby corrected as shown below:

In The Claims:

- Col. 51 Claim 5 line 46: Delete "seciuence" and replace it with --sequence--.
- Col. 51 Claim 5 line 47: Delete "nrotein" and replace it with --protein--.
- Col. 52 Claim 13 line 44: Delete "immunodeflciency" and replace it with --immunodeficiency--.

Signed and Sealed this

Twenty-second Day of July, 2008

JON W. DUDAS
*Director of the United States Patent and Trademark Office*

UNITED STATES PATENT AND TRADEMARK OFFICE
CERTIFICATE OF CORRECTION

PATENT NO. : 7,232,685 B2  Page 1 of 1
APPLICATION NO. : 10/323463
DATED : June 19, 2007
INVENTOR(S) : Eric M. Verdin et al.

It is certified that error appears in the above-identified patent and that said Letters Patent is hereby corrected as shown below:

Col. 1, line 15 should read

STATEMENT REGARDING FEDERALLY SPONSORED RESEARCH

--This invention was made with government support under grant nos. ROI-GM51671-05A2 awarded by the National Institutes of Health. The government has certain rights in this invention.--

Signed and Sealed this

Fifth Day of January, 2010

David J. Kappos
*Director of the United States Patent and Trademark Office*

UNITED STATES PATENT AND TRADEMARK OFFICE
CERTIFICATE OF CORRECTION

PATENT NO. : 7,232,685 B2 Page 1 of 1
APPLICATION NO. : 10/323463
DATED : June 19, 2007
INVENTOR(S) : Eric M. Verdin et al.

It is certified that error appears in the above-identified patent and that said Letters Patent is hereby corrected as shown below:

On the title page item [73], Delete "The Regents of the University of California" and it should read --The J. David Gladstone Institutes--.

Signed and Sealed this

Thirteenth Day of July, 2010

David J. Kappos
*Director of the United States Patent and Trademark Office*

SEQUENCE LISTING

```
<160> NUMBER OF SEQ ID NOS: 50

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gtggcgcccg aacagggacc                                           20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ccgtcgagat ccgttcacta                                           20

<210> SEQ ID NO 3
<211> LENGTH: 23
<212> TYPE: DNA
<213> ORGANISM: Artificial Sequence
<220> FEATURE:
<223> OTHER INFORMATION: primer
```

-continued

```
<400> SEQUENCE: 3
gctaattcac tcccaacgaa gac                                              23

<210> SEQ ID NO 4
<211> LENGTH: 23
<212> TYPE: DNA
<213> ORGANISM: Artificial Sequence
<220> FEATURE:
<223> OTHER INFORMATION: primer

<400> SEQUENCE: 4
gcttcttcta ccttctcttg ctc                                              23

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
gcccgtctgt tgtatgactc tg                                               22

<210> SEQ ID NO 6
<211> LENGTH: 23
<212> TYPE: DNA
<213> ORGANISM: Artificial Sequence
<220> FEATURE:
<223> OTHER INFORMATION: primer

<400> SEQUENCE: 6
cgccactgct agagttttc cac                                               23

<210> SEQ ID NO 7
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 16
<223> OTHER INFORMATION: s = G or C

<400> SEQUENCE: 7
agacagaagc attctsagaa                                                  20

<210> SEQ ID NO 8
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 10
<223> OTHER INFORMATION: n = A or G or C or T or unknown or other
<220> FEATURE:
<221> NAME/KEY: misc_feature
<222> LOCATION: 18
<223> OTHER INFORMATION: s = G or C

<400> SEQUENCE: 8
atcacaaagn agtttctsag aat                                              23

<210> SEQ ID NO 9
<211> LENGTH: 22
```

```
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 4
<223> OTHER INFORMATION: s = G or C
<220> FEATURE:
<221> NAME/KEY: misc_feature
<222> LOCATION: 7
<223> OTHER INFORMATION: w = A or T
<220> FEATURE:
<221> NAME/KEY: misc_feature
<222> LOCATION: 14
<223> OTHER INFORMATION: n = A or G or T or C or unknown or other
<220> FEATURE:
<221> NAME/KEY: misc_feature
<222> LOCATION: 17
<223> OTHER INFORMATION: k = G or T

<400> SEQUENCE: 9
tttsatwgag cagnttkgaa ac                                              22

<210> SEQ ID NO 10
<211> LENGTH: 23
<212> TYPE: DNA
<213> ORGANISM: Artificial Sequence
<220> FEATURE:
<223> OTHER INFORMATION: primer
<220> FEATURE:
<221> NAME/KEY: misc_feature
<222> LOCATION: 13
<223> OTHER INFORMATION: m = A or C
<220> FEATURE:
<221> NAME/KEY: misc_feature
<222> LOCATION: 16
<223> OTHER INFORMATION: n = A or G or T or C or unknown or other
<220> FEATURE:
<221> NAME/KEY: misc_feature
<222> LOCATION: 23
<223> OTHER INFORMATION: w = A or T

<400> SEQUENCE: 10
aaagagtgtt tcmaanctgc tcw                                             23

<210> SEQ ID NO 11
<211> LENGTH: 25
<212> TYPE: DNA
<213> ORGANISM: Artificial Sequence
<220> FEATURE:
<223> OTHER INFORMATION: primer

<400> SEQUENCE: 11
aggcaagctt tattgaggct taagc                                           25

<210> SEQ ID NO 12
<211> LENGTH: 24
<212> TYPE: DNA
<213> ORGANISM: Artificial Sequence
<220> FEATURE:
<223> OTHER INFORMATION: primer

<400> SEQUENCE: 12
tcccagctac tcgggaggct gagg                                            24

<210> SEQ ID NO 13
<211> LENGTH: 21
<212> TYPE: DNA
<213> ORGANISM: Artificial Sequence
<220> FEATURE:
```

```
<223> OTHER INFORMATION: primer

<400> SEQUENCE: 13
cacacacaag gctacttccc t                                              21

<210> SEQ ID NO 14
<211> LENGTH: 20
<212> TYPE: DNA
<213> ORGANISM: Artificial Sequence
<220> FEATURE:
<223> OTHER INFORMATION: primer
<220> FEATURE:
<221> NAME/KEY: modified_base
<222> LOCATION: 11
<223> OTHER INFORMATION: n = inosine

<400> SEQUENCE: 14
gccactcccc ngtcccgccc                                                20

<210> SEQ ID NO 15
<211> LENGTH: 24
<212> TYPE: DNA
<213> ORGANISM: Artificial Sequence
<220> FEATURE:
<223> OTHER INFORMATION: primer

<400> SEQUENCE: 15
gagccctcag atgctgcata taag                                           24

<210> SEQ ID NO 16
<211> LENGTH: 23
<212> TYPE: DNA
<213> ORGANISM: Artificial Sequence
<220> FEATURE:
<223> OTHER INFORMATION: primer

<400> SEQUENCE: 16
aactagggaa cccactgctt aag                                            23

<210> SEQ ID NO 17
<211> LENGTH: 30
<212> TYPE: DNA
<213> ORGANISM: Artificial Sequence
<220> FEATURE:
<223> OTHER INFORMATION: probe
<220> FEATURE:
<221> NAME/KEY: misc_feature
<222> LOCATION: 1
<223> OTHER INFORMATION: n = 5'- 6FAM-A
<220> FEATURE:
<221> NAME/KEY: misc_feature
<222> LOCATION: 30
<223> OTHER INFORMATION: n = 3'-TAMRA-T

<400> SEQUENCE: 17
ncactacttg aagcactcaa ggcaagcttn                                     30

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
tcgctttcag gtccctgttc g                                              21
```

-continued

```
<210> SEQ ID NO 19
<211> LENGTH: 28
<212> TYPE: DNA
<213> ORGANISM: Artificial Sequence
<220> FEATURE:
<223> OTHER INFORMATION: primer

<400> SEQUENCE: 19
ccatcgatgc caccatggag ccagtaga                                     28

<210> SEQ ID NO 20
<211> LENGTH: 17
<212> TYPE: DNA
<213> ORGANISM: Artificial Sequence
<220> FEATURE:
<223> OTHER INFORMATION: primer

<400> SEQUENCE: 20
agggtgtcgc cctcgaa                                                 17

<210> SEQ ID NO 21
<211> LENGTH: 21
<212> TYPE: DNA
<213> ORGANISM: Artificial Sequence
<220> FEATURE:
<223> OTHER INFORMATION: primer

<400> SEQUENCE: 21
gtgtgcccgt ctgttgtgtg a                                            21

<210> SEQ ID NO 22
<211> LENGTH: 21
<212> TYPE: DNA
<213> ORGANISM: Artificial Sequence
<220> FEATURE:
<223> OTHER INFORMATION: primer

<400> SEQUENCE: 22
gccactgcta gagattttcc a                                            21

<210> SEQ ID NO 23
<211> LENGTH: 18
<212> TYPE: DNA
<213> ORGANISM: Artificial Sequence
<220> FEATURE:
<223> OTHER INFORMATION: probe

<400> SEQUENCE: 23
ctggtaacta gagatccc                                                18

<210> SEQ ID NO 24
<211> LENGTH: 21
<212> TYPE: DNA
<213> ORGANISM: Artificial Sequence
<220> FEATURE:
<223> OTHER INFORMATION: primer

<400> SEQUENCE: 24
ggtcttgtag ttgccgtcgt c                                            21

<210> SEQ ID NO 25
<211> LENGTH: 19
<212> TYPE: DNA
<213> ORGANISM: Artificial Sequence
<220> FEATURE:
<223> OTHER INFORMATION: primer
```

```
<400> SEQUENCE: 25
gaagaagatg gtgcgctcc                                              19

<210> SEQ ID NO 26
<211> LENGTH: 22
<212> TYPE: DNA
<213> ORGANISM: Artificial Sequence
<220> FEATURE:
<223> OTHER INFORMATION: primer

<400> SEQUENCE: 26
ttgcctgtac tgggtctctc tg                                          22

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
attccatgca ggctcacagg                                             20

<210> SEQ ID NO 28
<211> LENGTH: 23
<212> TYPE: DNA
<213> ORGANISM: Artificial Sequence
<220> FEATURE:
<223> OTHER INFORMATION: primer

<400> SEQUENCE: 28
gtgtaacaag cgggtgttct ctc                                         23

<210> SEQ ID NO 29
<211> LENGTH: 38
<212> TYPE: DNA
<213> ORGANISM: Artificial Sequence
<220> FEATURE:
<223> OTHER INFORMATION: linker

<400> SEQUENCE: 29
gacccgggag atctgaattc agtggcacag cagttagg                         38

<210> SEQ ID NO 30
<211> LENGTH: 26
<212> TYPE: DNA
<213> ORGANISM: Artificial Sequence
<220> FEATURE:
<223> OTHER INFORMATION: linker

<400> SEQUENCE: 30
cctaactgct gtgccactga attcag                                      26

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
gacccgggag atctgaattc                                             20

<210> SEQ ID NO 32
<211> LENGTH: 18
```

```
<212> TYPE: DNA
<213> ORGANISM: Artificial Sequence
<220> FEATURE:
<223> OTHER INFORMATION: primer

<400> SEQUENCE: 32
agtggcacag cagttagg                                                    18

<210> SEQ ID NO 33
<211> LENGTH: 69
<212> TYPE: DNA
<213> ORGANISM: Homo sapiens

<400> SEQUENCE: 33
atgtgtgcgt tcaactcaca gagtttaacc tttcttttcg tagagcagtg aagggctaa      60 ttcactccc                                                             69

<210> SEQ ID NO 34
<211> LENGTH: 48
<212> TYPE: DNA
<213> ORGANISM: Homo sapiens

<400> SEQUENCE: 34
atgtgtgcgt tcaactcaca gagtttaacc tttcttttcg tagagcag                  48

<210> SEQ ID NO 35
<211> LENGTH: 69
<212> TYPE: DNA
<213> ORGANISM: Homo sapiens

<400> SEQUENCE: 35
agctcctgac tatgataaag tatcttgtga aaaccaatg ttactgcttg gaagggctaa      60
ttcactccc                                                             69

<210> SEQ ID NO 36
<211> LENGTH: 48
<212> TYPE: DNA
<213> ORGANISM: Homo sapiens

<400> SEQUENCE: 36
agctcctgac tatgataaag tatcttgtga aaaccaatg ttactgct                   48

<210> SEQ ID NO 37
<211> LENGTH: 69
<212> TYPE: DNA
<213> ORGANISM: Homo sapiens

<400> SEQUENCE: 37
cggctcactg cagcctccgc ctctcgaatt caattctgtc tcagcctctg gaagggctaa     60
ttcactccc                                                             69

<210> SEQ ID NO 38
<211> LENGTH: 48
<212> TYPE: DNA
<213> ORGANISM: Homo sapiens

<400> SEQUENCE: 38
cggctcactg cagcctccgc ctctcgaatt caattctgtc tcagcctc                  48

<210> SEQ ID NO 39
<211> LENGTH: 69
<212> TYPE: DNA
```

<210> SEQ ID NO 39
<211> LENGTH: 69
<212> TYPE: DNA
<213> ORGANISM: Homo sapiens

<400> SEQUENCE: 39

```
ctgtgatttg aatgcacaca tcacaaagaa gtttctcaga atgcttcttg gaagggctaa        60
ttcactccc                                                                69
```

<210> SEQ ID NO 40
<211> LENGTH: 48
<212> TYPE: DNA
<213> ORGANISM: Homo sapiens

<400> SEQUENCE: 40

```
ctgtgatttg aatgcacaca tcacaaagaa gtttctcaga atgcttct                     48
```

<210> SEQ ID NO 41
<211> LENGTH: 69
<212> TYPE: DNA
<213> ORGANISM: Homo sapiens

<400> SEQUENCE: 41

```
gagttgacaa aggtaaaaca gatttttaa aaatcagttg tttatatttg gaagggctaa         60
ttcactccc                                                                69
```

<210> SEQ ID NO 42
<211> LENGTH: 48
<212> TYPE: DNA
<213> ORGANISM: Homo sapiens

<400> SEQUENCE: 42

```
gagttgacaa aggtaaaaca gatttttaa aaatcagttg tttatatt                      48
```

<210> SEQ ID NO 43
<211> LENGTH: 69
<212> TYPE: DNA
<213> ORGANISM: Homo sapiens

<400> SEQUENCE: 43

```
ctgtgatttg aatgcacaca tcacaaagga gtttctgaga atgcttcttg gaagggctaa        60
ttcactccc                                                                69
```

<210> SEQ ID NO 44
<211> LENGTH: 48
<212> TYPE: DNA
<213> ORGANISM: Homo sapiens

<400> SEQUENCE: 44

```
ctgtgatttg aatgcacaca tcacaaagga gtttctgaga atgcttct                     48
```

<210> SEQ ID NO 45
<211> LENGTH: 69
<212> TYPE: DNA
<213> ORGANISM: Homo sapiens

<400> SEQUENCE: 45

```
ttcgtaggag aactagacag aatgattctc agaaactact ttgtgatgtg gaagggctaa        60
ttcactccc                                                                69
```

<210> SEQ ID NO 46
<211> LENGTH: 48
<212> TYPE: DNA
<213> ORGANISM: Homo sapiens

<400> SEQUENCE: 46
ttcgtaggag aactagacag aatgattctc agaaactact ttgtgatg          48

<210> SEQ ID NO 47
<211> LENGTH: 205
<212> TYPE: DNA
<213> ORGANISM: Homo sapiens

<400> SEQUENCE: 47
aaagagtgtt tccaagctgc tctgtcaaaa ggaaggttct tctctgttag gtgagtgcat    60
acgtcataaa ggagtttctg agaattcttc tgtctagttc ttatttgtag acgtttcctt   120
tctcaccttg ggcctgaaag cgctcgaaat atccacttcc agatagtaca gaaatagtga   180
ttcaaacctg gaagggctaa ttcac                                         205

<210> SEQ ID NO 48
<211> LENGTH: 230
<212> TYPE: DNA
<213> ORGANISM: Homo sapiens
<220> FEATURE:
<221> NAME/KEY: misc_feature
<222> LOCATION: 84
<223> OTHER INFORMATION: n = A,T,C or G

<400> SEQUENCE: 48 gacccttta gtcagtgtgg aaaatctcta gcaaaagggt gtttcaaacc tgctctatga    60
aagggaatgt tcaactctgt gacnttgaat gcaaatatca caagaagtt actgggaatg   120 ctgctgtctg cttttttatat gtaatcccgt ttccaacgaa atcctcaaag ctagacaaat   180
atccacttgc agattccaca aaagagtgtt tcaaatctg ctcaatcaaa              230

<210> SEQ ID NO 49
<211> LENGTH: 570
<212> TYPE: DNA
<213> ORGANISM: Homo sapiens

<400> SEQUENCE: 49
tctggtccct ggccctggtg tgtagttctg ccaatcaggg aagtagcctt gtgtgtggta    60
gacccacaga tcaagaatat cttgtctgtt ctgggagtga actagcctt ccacctgcat   120 gtggaaattt tgagcgcttt gaggcctatt gtggaaaagg aaatatgttc acataaaagc   180
tacacagaag cattctgaaa aacgtctttg tgatgagtgc attcatctca cagagttgat   240
cctttctttt tattcagcag ttttgaaaca ctccttttag agaatctgca agtagatatt   300
tggagcgcgt tgaggcctac catggaaaag caaatatctt cacataaaaa ctacacagaa   360
atattctcag aaactacttt gtgatatgtg tgttcaattc acagagttga acctttcttt   420
tcattgagca gttttgaaaa actgcttttc tagaatctgc ttgtggatat ttggagctct   480
ttgaggaatt cattgtcaat gggatatctt catatacaaa ctagccagaa gcattctcag   540
aaactacttt gtgatcctga attccagcac                                    570

<210> SEQ ID NO 50
<211> LENGTH: 569
<212> TYPE: DNA
<213> ORGANISM: Homo sapiens
<220> FEATURE:
<221> NAME/KEY: misc_feature
<222> LOCATION: 535, 544
<223> OTHER INFORMATION: n = A,T,C or G

```
<400> SEQUENCE: 50
agtccctggc cctggtgtgt agttctgcca atcagggaag tagccttgtg tgtggtagac        60
ccacagatca agaatatctt gtcttttctg ggagtaaatt agcccttcca gatattaact       120
tttcaaacat aggccgcaca gtgatccaaa tatgtacctt acagatactt caaaaagact       180
gtttccaacc tgctcaatga aaagaaagtt tcaactgtgt gagtggaatg caaacatcac       240
aaagaagttt ctcagaatgc ccctgtcaac tttatatgtg aagatattgc cttttccaca       300
aaacgcctca aaccattcca aatatccatt tgcagattcc acaaaaagac tgtttccaaa       360
ctgctcaacc aaaaaaaggt tcaactctgt gagatgaatg cacccatcac aaagaagttt       420
ttcagaaagc ttctgtttag tttttatgtg aagatatttc cttttcact ataggcttca        480 aagcactcca cacatccatt tgcagattct acaaaagagt gtttccaatc tgctncctga       540
attncagcac actggcggcc gttactagt                                         569
```